United States Patent [19]

Ho

[11] 4,365,514
[45] Dec. 28, 1982

[54] METHOD AND APPARATUS FOR NON-DESTRUCTIVE INSPECTION OF TIRES

[75] Inventor: Morris D. Ho, Walnut Creek, Calif.

[73] Assignee: Bandag Incorporated, Muscatine, Iowa

[21] Appl. No.: 262,706

[22] Filed: May 11, 1981

Related U.S. Application Data

[62] Division of Ser. No. 31,962, Apr. 19, 1979, Pat. No. 4,285,235.

[51] Int. Cl.³ .............................................. G01M 3/24
[52] U.S. Cl. .................................... 73/592; 73/40.5 A
[58] Field of Search ....................... 73/49, 40.5 A, 592, 73/146

[56] References Cited

U.S. PATENT DOCUMENTS 3,192,516  6/1965  Simpkins et al. ................. 73/40.5 A
3,222,635 12/1965  Simpkins et al. ................. 73/40.5 A

FOREIGN PATENT DOCUMENTS 1174048 12/1969 United Kingdom ............ 73/40.5 A

Primary Examiner—Anthony V. Ciarlante
Attorney, Agent, or Firm—Cushman, Darby & Cushman

[57] ABSTRACT

A pulsed through-transmission ultrasonic non-destructive inspection of the internal structure in a tire wall is effected. The transmitted acoustic signals preferably have a frequency of at least 40 KHz, are transduced to electrical form, amplified with a relatively long time constant AGC, rectified and integrated during only the initial or leading edge portions of each pulse or burst. The resulting integrated analog signal values thus provided have relative magnitudes which may be displayed or otherwise processed to detect structural anomalies within the tire wall. If plural acoustic transmitters are utilized, they are preferably multiplexed such that only a single transducer is activated at a given time. Air leaks from the pressurized tire under test are also detected by detecting ultrasonic signals generated by escaping air.

9 Claims, 21 Drawing Figures

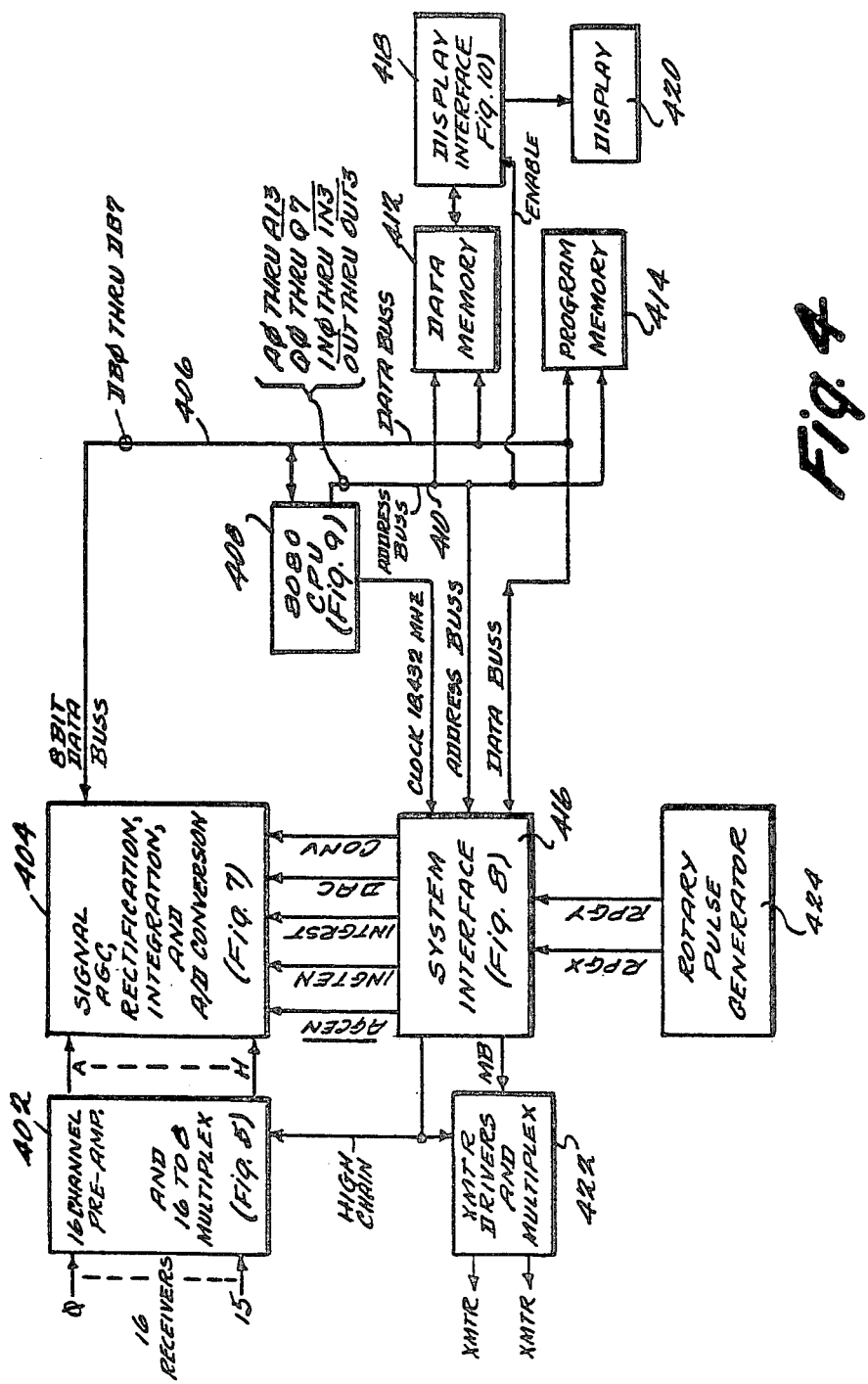

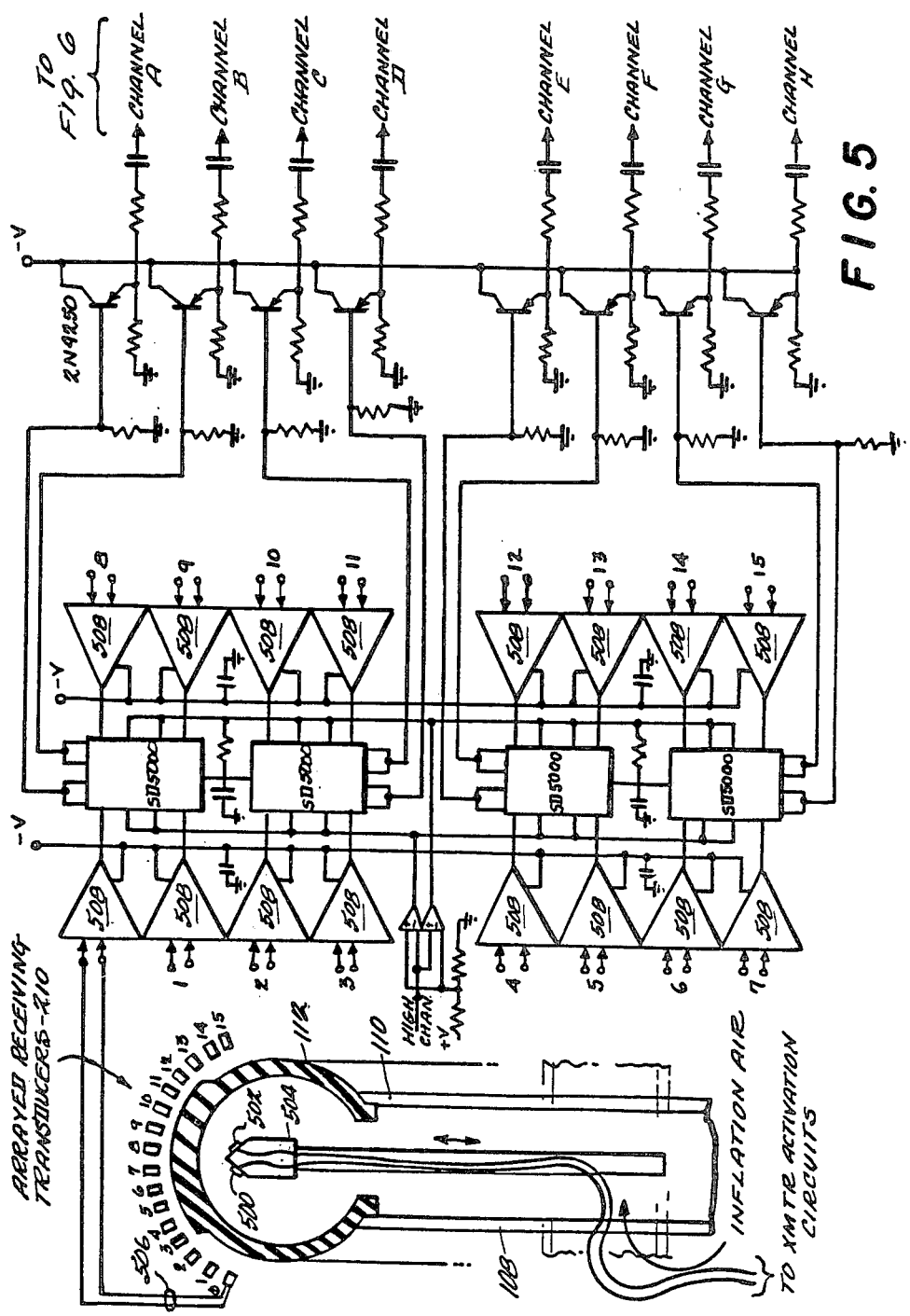

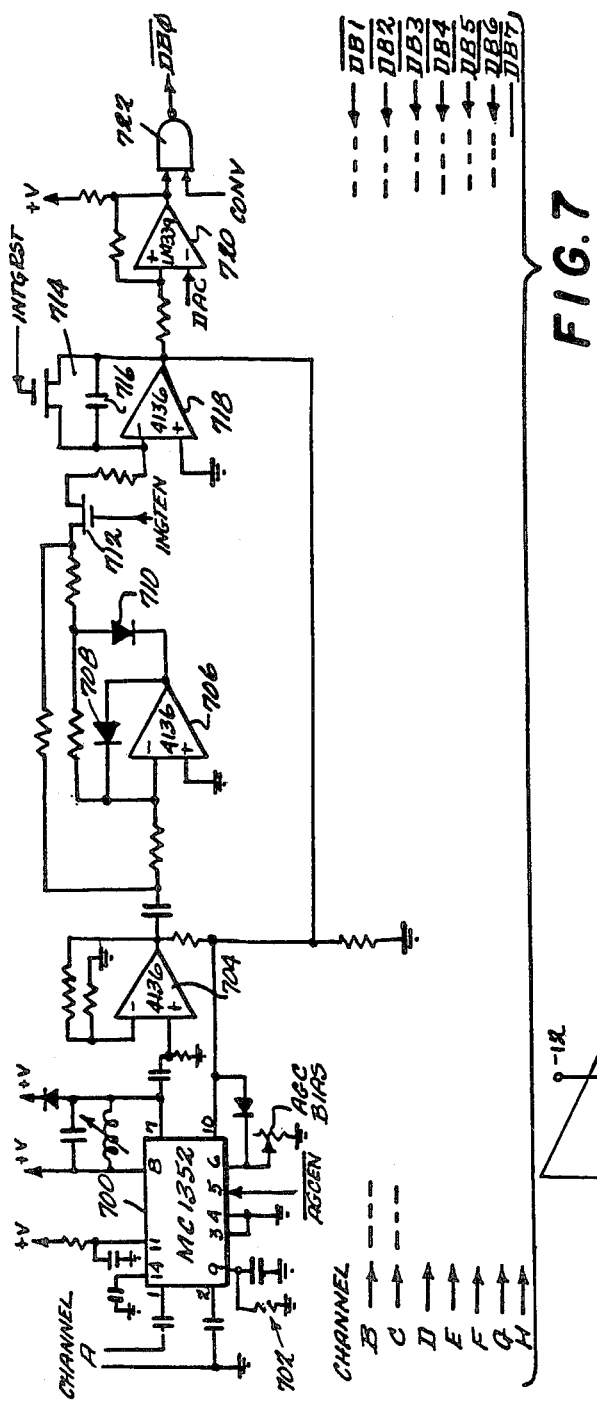
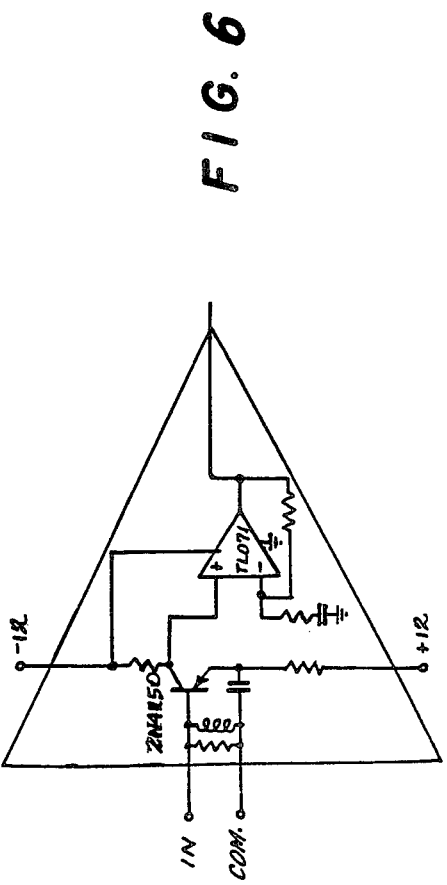
FIG. 7
FIG. 6

METHOD AND APPARATUS FOR NON-DESTRUCTIVE INSPECTION OF TIRES

This application is a division of my earlier copending application Ser. No. 31,962 filed Apr. 19, 1979 now U.S. Pat. No. 4,285,235 dated Aug. 25, 1981.

This invention is generally directed to methods and apparatus for non-destructive inspection or rubber tires. Such inspection techniques may also be combined with conventional tire buffing operations in accordance with this invention.

The invention here claimed is directed to certain air leak detection features of the preferred embodiment. The mechanical features, per se are the sole invention of Doyle L. Dugger and are claimed in commonly assigned copending application No. 31,961 filed Apr. 19, 1979 now U.S. Pat. No. 4,266,428 dated May 12, 1981 and in a divisional application Ser. No. 233,967 filed Feb. 12, 1981. The combination of mechanical and electrical features, is the joint invention of myself and Doyle L. Dugger and is claimed in commonly assigned copending application No. 31,963 filed Apr. 19, 1979 now U.S. Pat. No. 4,275,589 dated June 30, 1981.

There has long been an urgent need for cost effective, efficient, non-destructive inspection (NDI) of rubber tire casings. There are obvious safety benefits to be had by such techniques if they can be efficiently and rapidly practiced. There are also potential economic benefits. For example, during tire retreading operations, a defective tire carcass can be discarded before wasting further expenditures of time and money if it can be accurately, efficiently and quickly detected.

In fact, the need for improved NDI methods and apparatus relating to the testing of tire casings is so great that the Army Materials and Mechanics Research Center has sponsored special symposia devoted entirely to this subject in 1973, 1974, 1976 and 1978. The proceedings of the first three of these symposia have now been published and are available from the National Technical Information Service. They each include a complete chapter on ultrasonic tire testing as well as other chapters devoted to different tire testing procedures (e.g. holographic, infrared and X-ray). There are also many prior art patents relating generally to the use of ultrasonic waves to non-destructively test pneumatic tire casings. For example: U.S. Pat. Nos. 2,345,679—Linse (1944), 2,378,237—Morris (1945), 3,336,794—Wysoczanski et al (1967), 3,604,249—Wilson (1971), 3,815,407—Lavery (1974), 3,882,717—McCauley (1975), 4,059,989—Halsey (1977).

There are also several prior art patents relating to mechanical structures for chucking or otherwise physically handling pneumatic tire casings during various types of non-destructive testing or manufacturing processes. For example: U.S. Pat. Nos. 2,695,520—Karsai (1954), 3,550,443—Sherkin (1970), 3,948,094—Honlinter (1976), 4,023,407—Vanderzee (1977).

Although a wide variety of non-destructive ultrasonic tests have been performed on tires in the past are shown by these prior art patents, they have each suffered serious deficiencies and have failed to achieve widespread acceptance in commercial practice. Some of the prior art approaches have required a liquid coupling medium on one or both sides of the tire wall under test. Some prior testing procedures use a so-called "pulse-echo" approach which gives rise to a rather complex pattern of echos due to normal internal tire structures as well as for abnormal structures. Many have used relatively low frequencies (e.g. 25 Khz) with resulting severe interference from normal ambient acoustic sources while others have used extremely high frequencies (e.g. 2 Mhz) with resulting rapid signal attenuation. Some have used continuous ultrasonic waves resulting in a confusing pattern of standing waves and the like while others have looked for envelope peaks in the received acoustic waves. Others have used individual pulses of acoustic signals for each tire testing site. In some cases the peak received envelope magnitude has been used to reach final data values. Some have also attempted to test an inflated tire carcass (but sometimes causing the acoustic signals to pass through two tire walls so as to keep all transducers external to the tire) although most have attempted to test a noninflated tire carcass. There may have been other techniques as well.

It has now been discovered that these earlier attempts at ultrasonic non-destructive inspection of tire casings can be considerably improved and made more commercially viable.

For example, it has been discovered that a pulse or burst transmission mode may be used to reduce standing waves or unwanted reverberation effects within the tire. Each burst comprises only a few (e.g. 100) cycles of acoustic signals providing a very low overall duty cycle and extremely efficient transducer operation. At the same time, it has been discovered that the envelope of received acoustic signals may be altered by internal reverberation, standing wave, wave cancellation or other irrelevant wave effects after the initial portion or rising edge of each burst is received. Accordingly, in the preferred embodiment of this invention, the received acoustic signals are passed through a gated receiver circuit such that only those signals within the initial portion of each burst are utilized.

Still further improvements may be possible in some circumstances by averaging readings taken at different frequencies thereby avoiding some possible adverse standing wave pattern effects and the like. Furthermore, non-linear analog-to-digital conversion techniques may be used to assist in recovering usable data.

In the presently preferred embodiment, plural transmitting acoustic transducers are located inside a revolving inflated tire so as to acoustically illuminate the entire inside tire surfaces under test. However, it has been discovered that peculiar wave cancellation, standing wave patterns or similar wave effects may distort readings if more than one transmitter is activated at a given time. Accordingly, the preferred embodiment includes multiplexing circuitry to insure that only a single transducer is activated at a given time.

Plural acoustic receiving transducers are arrayed about the outer tire walls so as to receive acoustic signals transmitted therethrough from the transmitting transducers located inside the tire. Each receiving transducer is preferably collimated and matched to the ambient air impedance with a cylindrical tube having an inner conical surface which tapers down to the sensing area of the actual receiving transducer. Such collimation helps to confine each receiver's output to represent acoustic signals transmitted through a limited area of the tire wall and further helps to reject interference from tread patterns and ambient noise. Flaws in the tires such as separations between cord layers and rubber layers or between various rubber layers attenuate the acoustic signals passing therethrough to a greater extent than when the acoustic signals pass through a normal section of the tire wall.

It has also been discovered that leaks in in a pressurized tire (i.e. air passing through the tire wall) can be detected with the same ultrasonic receiving transducers by noting an increase in received signal level over that encountered during passage by normal sections of the tire wall even while the ultrasonic transmitters are turned off.

Each of the receiving transducers is connected to its own signal processing channel albeit plural receivers may be multiplexed to share a common signal processing channel in synchronization with the multiplexing of the plural acoustic transmitters thereby minimizing the number of necessary signal processing channels. A relatively long term automatic gain controlled amplifier is incorporated in each signal processing channel so as to compensate for different average signal levels from tire-to-tire and from channel-to-channel, depending upon different average respective tire wall thicknesses. After AGC amplification, the received ultrasonic signals are rectified and integrated during a gated period on the rising edge of each burst. The resulting integrated values then truly represent the relative transmission capabilities of different successive sections of the tire wall under inspection. In one exemplary embodiment, successive observations at each tire wall position are averaged together to avoid potential standing wave null points and the like which might occur at some receiver locations for some particular frequency and tire geometry. Such values may be displayed on a CRT for visual inspection and detection of defects. Alternatively, such values may be digitized (possibly with a nonlinear exponential-law A-to-D process to enhance the effective signal-to-noise ratio at relatively low signal strengths) before display and/or process desired pattern recognition algorithms in a digital computer so as to automatically identify tire anomalies such as separations between layers.

It has also been discovered that improved operation results when the acoustic signals are of a moderately high frequency (e.g. greater than approximately 40 Khz and, in the preferred embodiment, 75 Khz). Such moderately high acoustic frequencies tend to avoid unwanted spurious indications caused by the usual ambient acoustic sources and, at the same time, provide relatively short wave lengths (e.g. approximately 1.5 inches or so in tire rubber) thereby improving the resolution of relatively small tire defects, yet without unnecessarily complicating the observed transmission readings by having a wave length so small that the signals may be affected by tire structure anomalies presenting no actual defect.

The averaging of received signal over several cycles during the leading edge of each burst improves the signal-to-noise ratio of the resulting measured values as does the use of a non-linear A to D process. The averaging of data taken at different frequencies may further enhance the results.

The use of an inflated tire in the preferred embodiment has been discovered to assist in maintaining a true running tire surface and thus avoids signal variations that might otherwise be caused by wobbling or other relative axial motions of the tire walls during rotation. The inflated tire is also useful in helping to at least partially stress the tire walls, as they will be stressed during normal use, and to open up leakage passageways through the tire walls so that they may be detected by ultrasonic detection of air passing therethrough. Approximately only five psi is needed to maintain a stable inflated tire structure. However, it has been discovered that improved signal transmission and overall performance occurs if the tire is inflated within the range of approximately 15-18 psi.

Although it may not be required, it is preferred that the outer treadwall of the tire under inspection first be buffed to present a uniform surface thus minimizing spurious defect indications that might otherwise be caused by tread patterns and/or by uneven wear spots or patterns in the outer treadwall surface of the tire. In this connection, the tire buffing apparatus and method may be advantageously employed in combination with the ultrasonic non-destructive testing method and apparatus to present a unified, convenient and efficient overall operation. Since such a buffing operation is necessarily involved in tire retreading operations anyway, this combination is particularly attractive where the tire carcasses are being inspected in preparation for retreading.

The ultrasonic bursts and receiver gating periods are preferably synchronized to occur at corresponding successive incremental positions of the rotating tire such that the final display or defect indication may be accurately located with respect to an index mark on the tire and/or tire mounting flange or the like.

These and other objects and advantages of this invention will be better appreciated by reading the following detailed description of the presently preferred exemplary embodiment in conjunction with the accompanying drawings, of which:

FIG. 4 is a block diagram of the ultrasonic NDI circuits which may be used in the NDI/buffer machines of FIGS. 1-3 or in a machine having only NDI capabilities;

Figure 7:
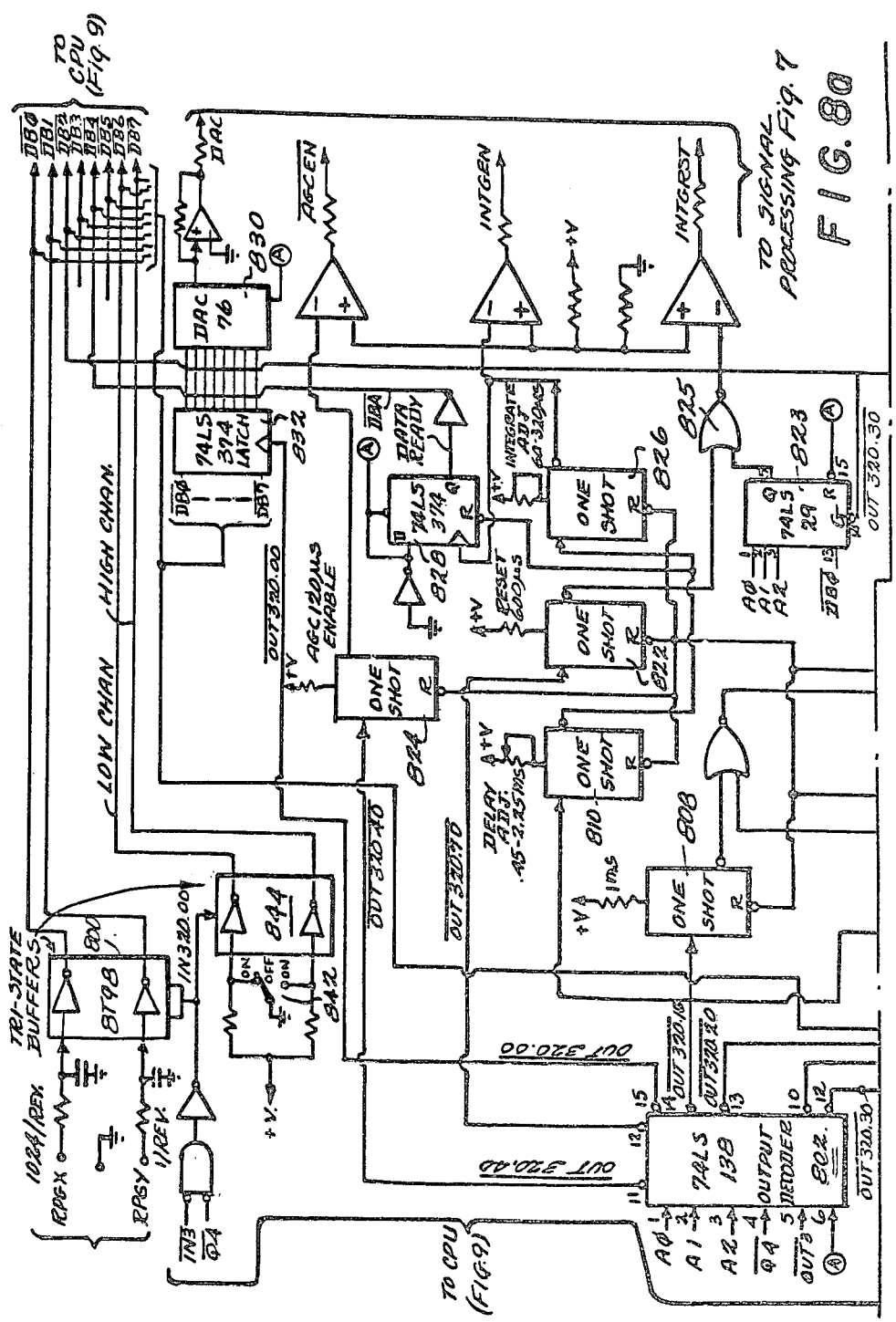
Figure 9:
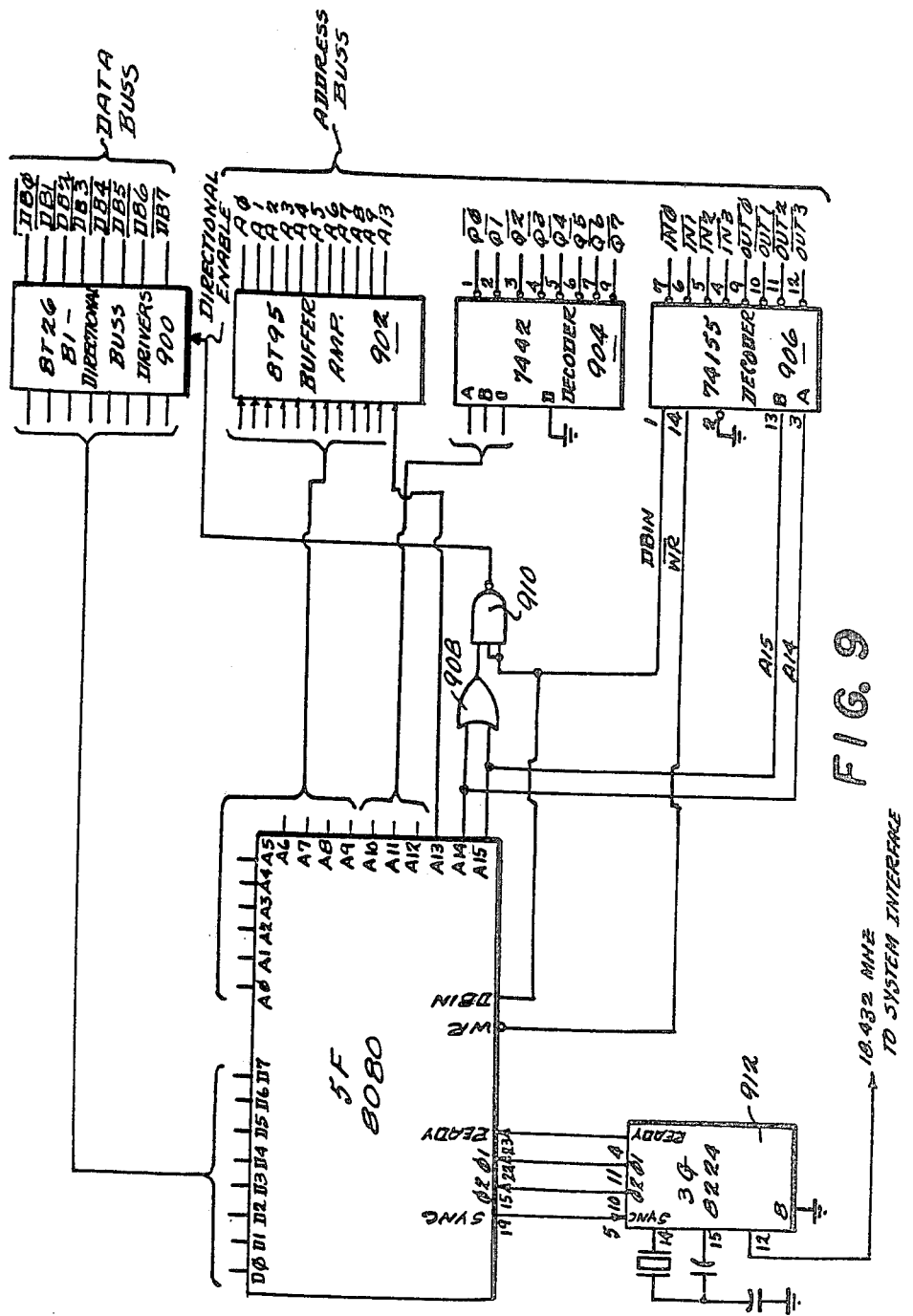
Figure 10:
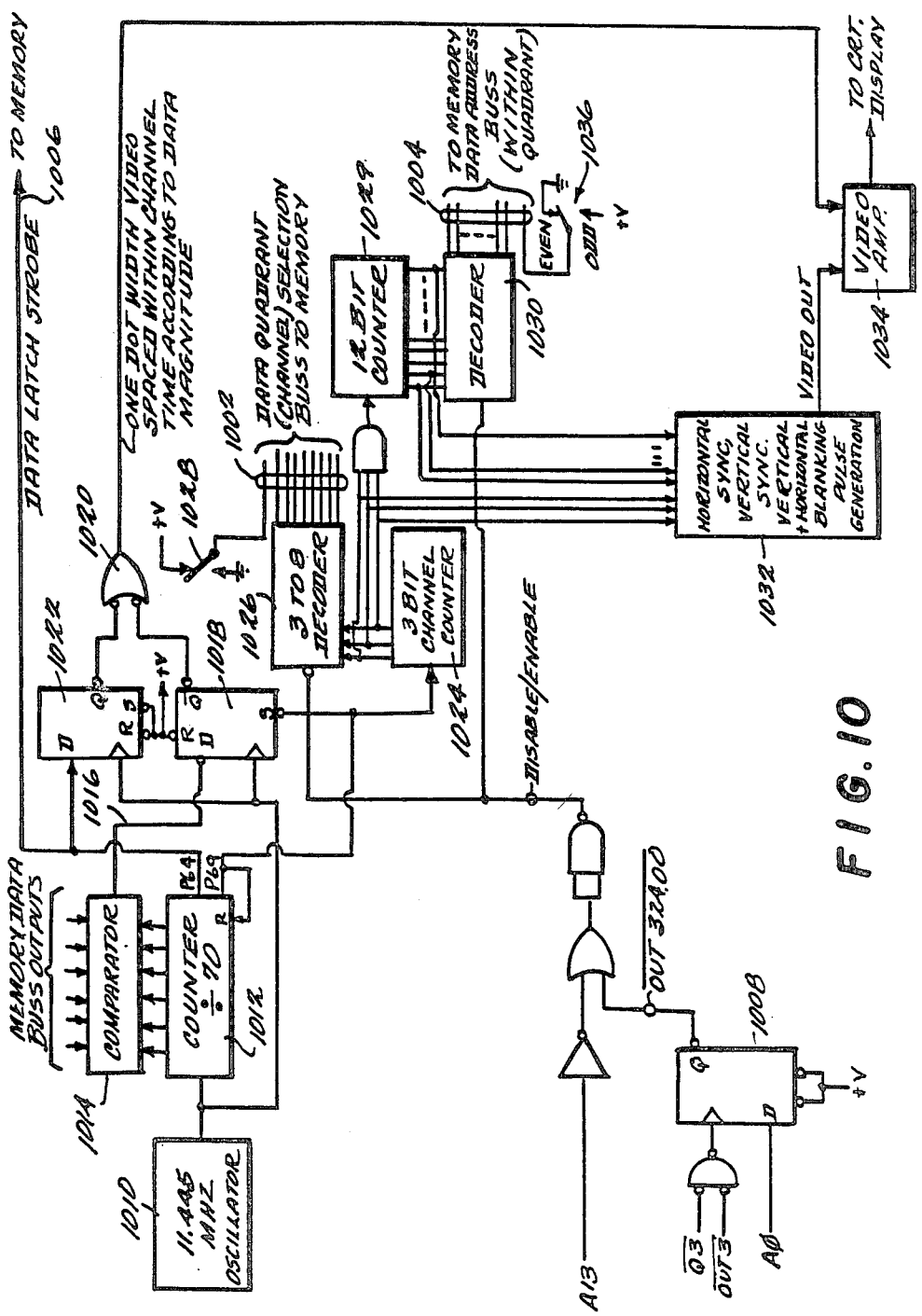
Figure 11:
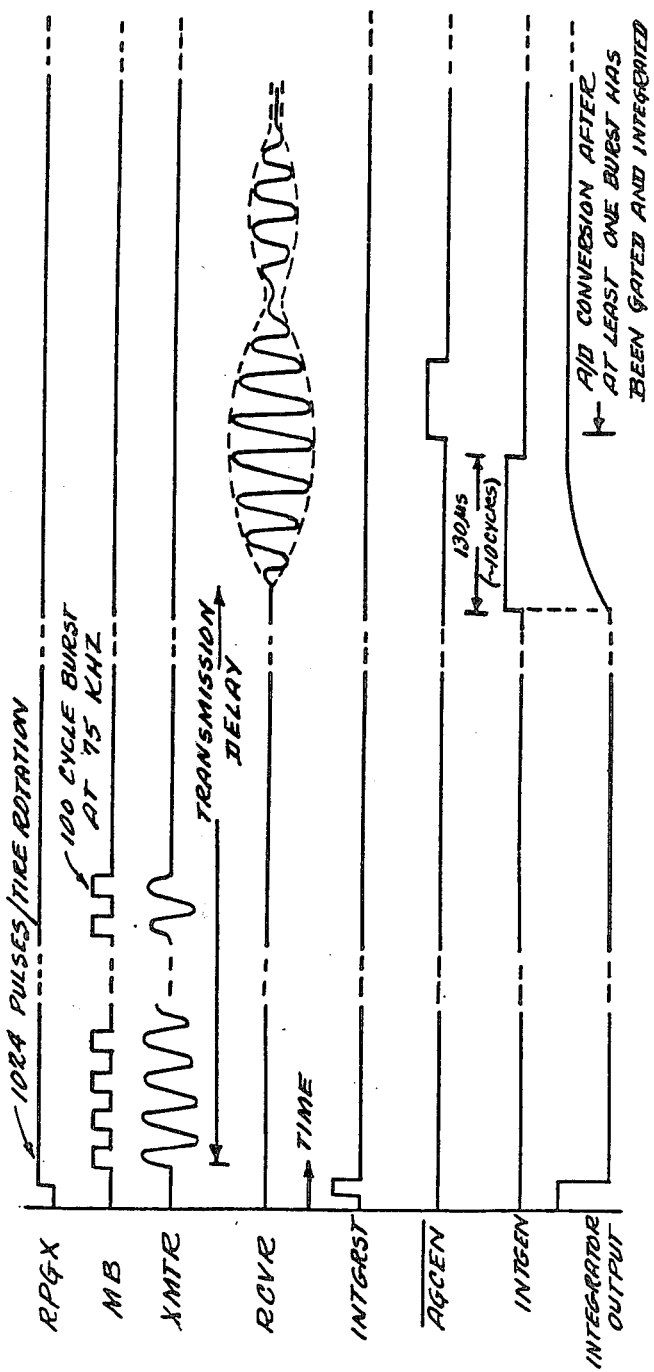
Figure 12:
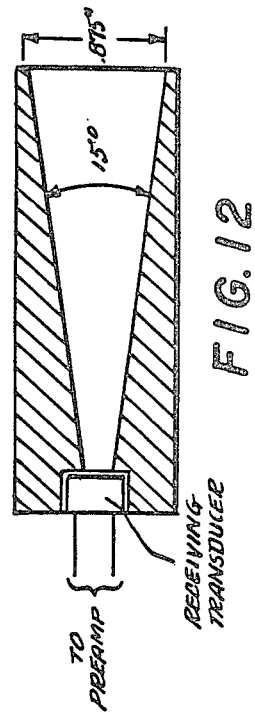
Figure 13:
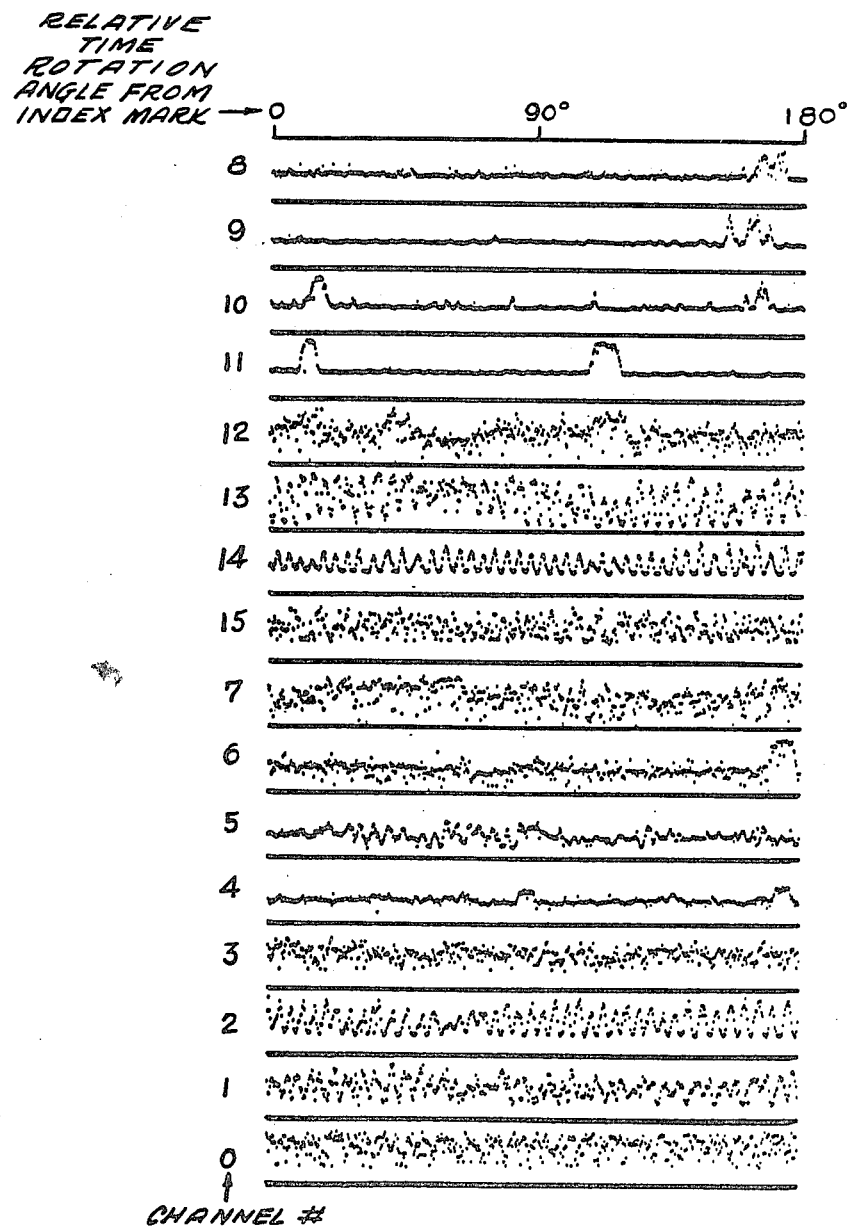
Figure 14:
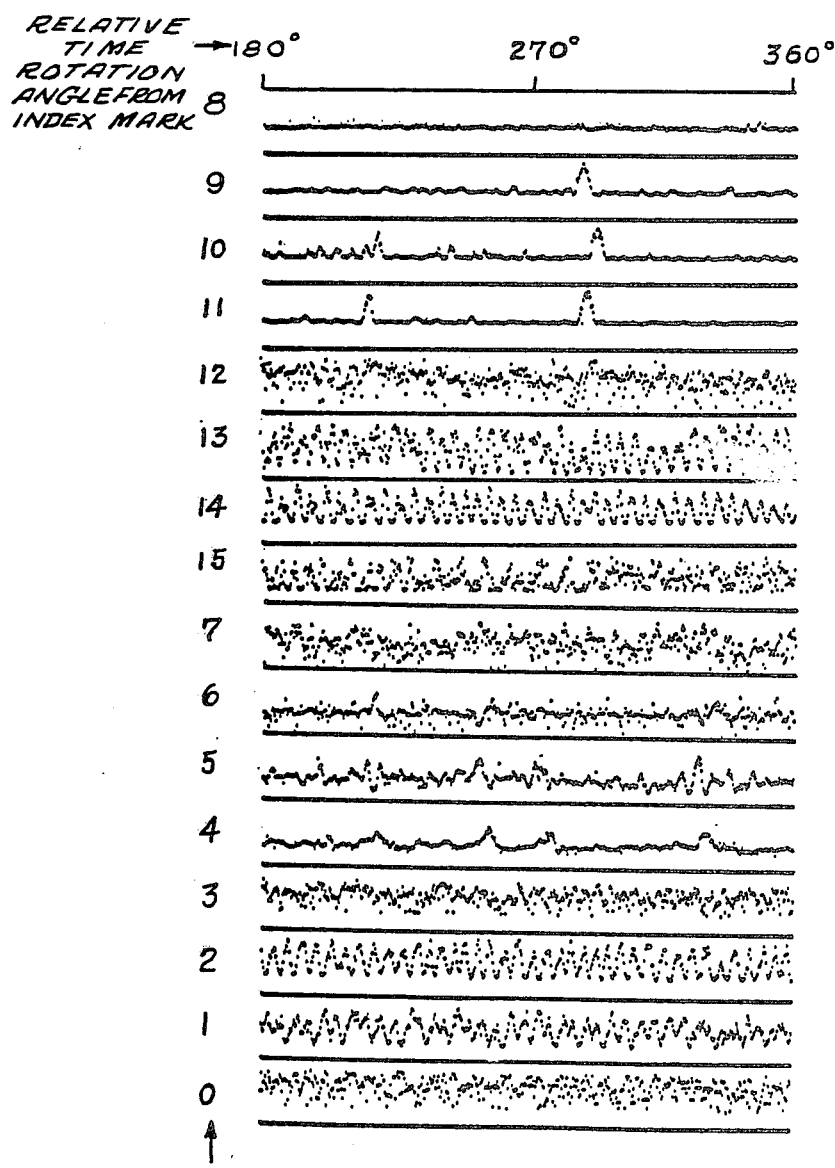
Figure 15:
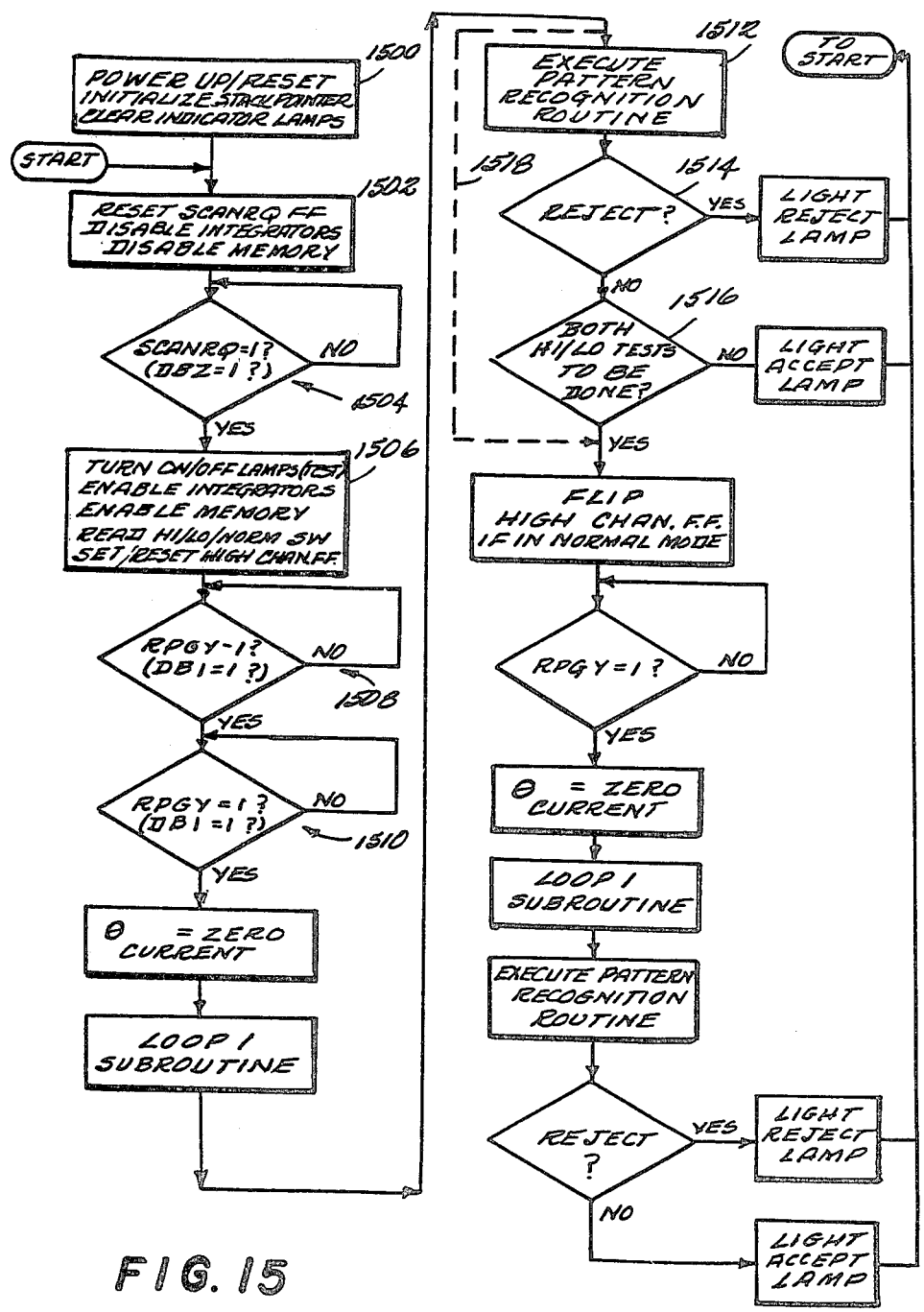
Figure 16:
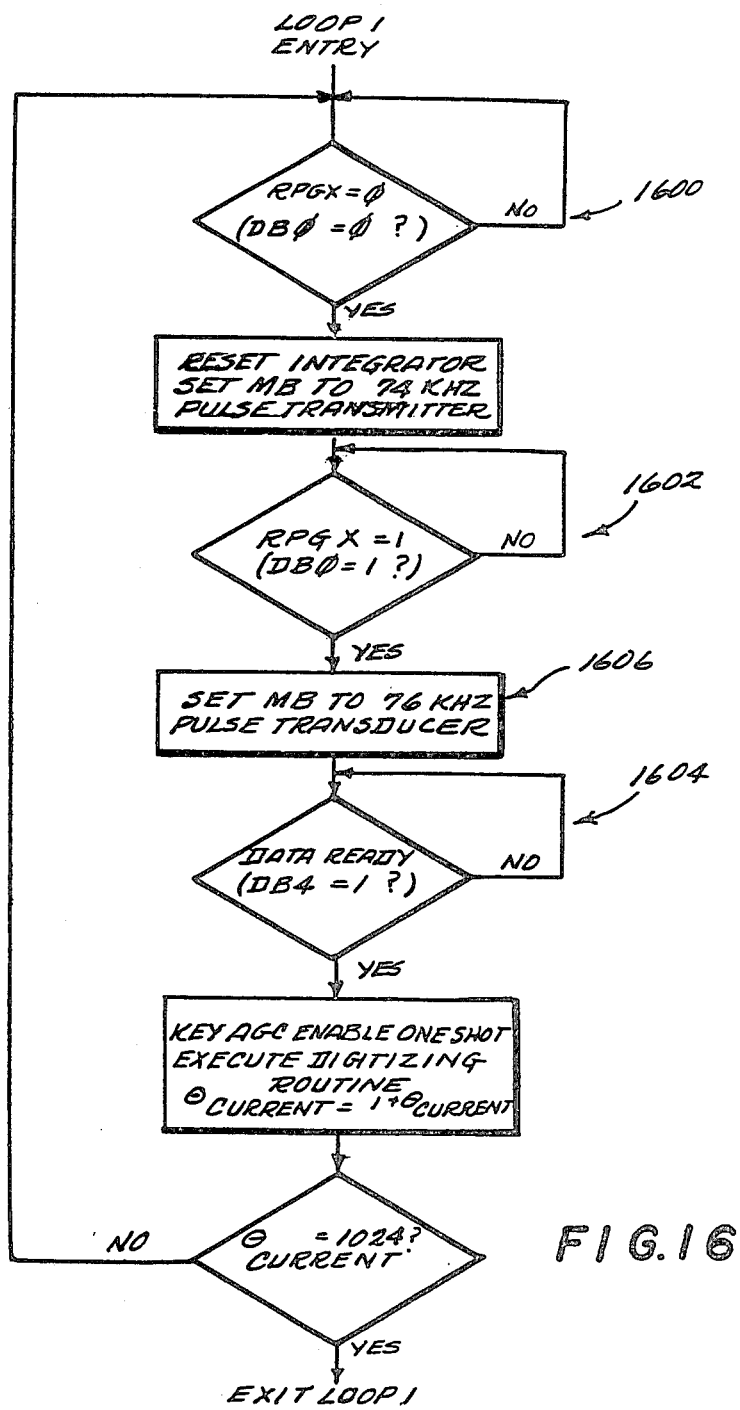
Figure 17:
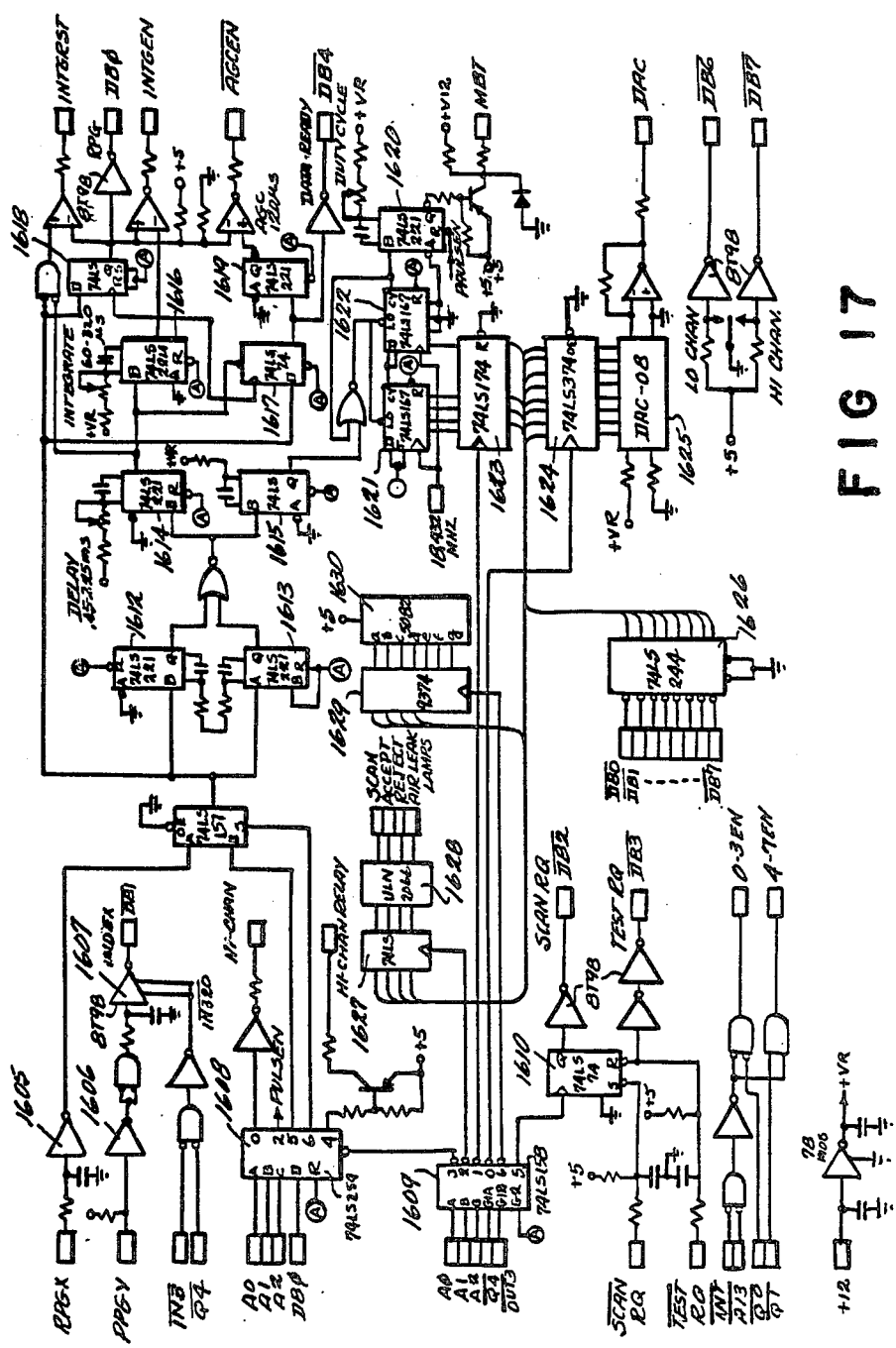
Figure 18:
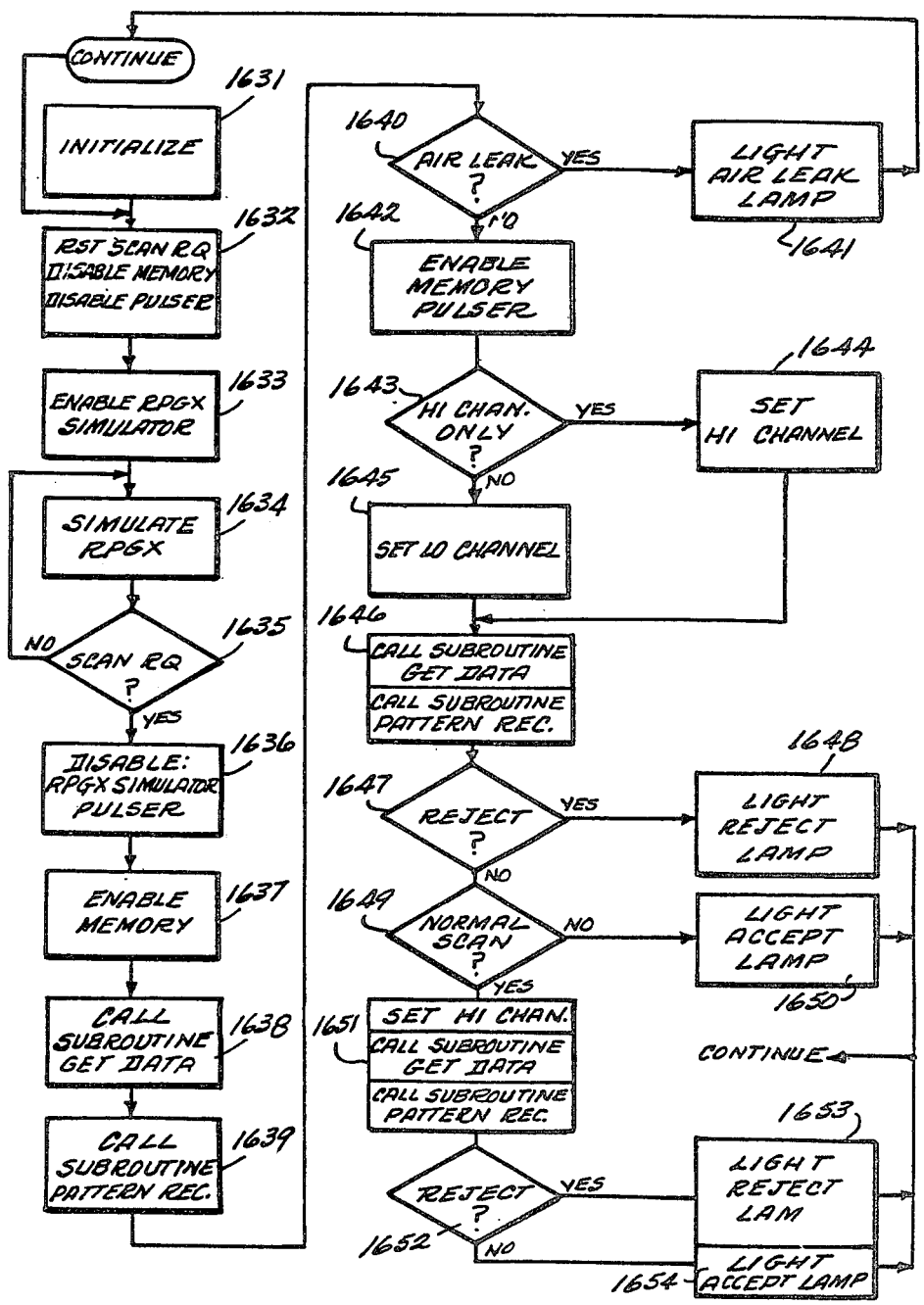
Figure 19A:
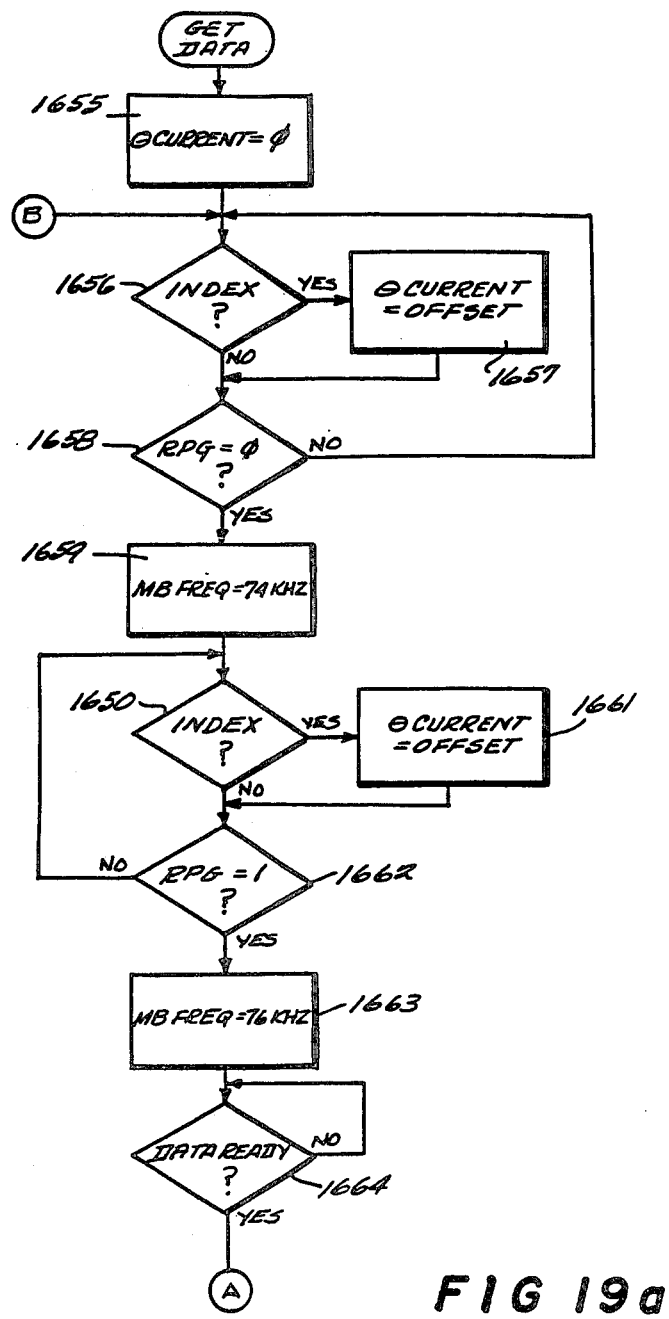
Figure 19B:
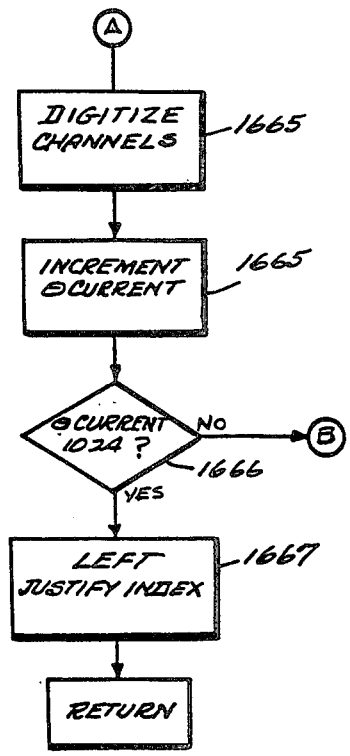

FIG. 5 includes a schematic showing of a tire wall section, acoustic transmitters and receivers and of the pre-amplifier and multiplexing circuitry shown in FIG. 4;

FIG. 6 is a detailed circuit diagram of the pre-amplifier shown in FIG. 5;

FIG. 7 is a detailed circuit diagram of a representative one of the signal processing channels shown in FIG. 4;

FIGS 8a and 8b comprise a detailed circuit diagram of the system interface shown in FIG. 4;

FIG. 9 is a detailed circuit diagram of the CPU or central processing unit shown in FIG. 4;

FIG. 10 is a detailed circuit diagram of the display interface shown in FIG. 4;

FIG. 11 is a schematic depiction of several representative wave forms useful in explaining the operation of the circuits shown in FIGS. 4-10;

FIG. 12 is a cross-sectional view of a collimater/impedance matching device used in each of the receiving transducers;

FIGS. 13 and 14 are tracings of CRT outputs obtained by non-destructively inspecting a buffed tire carcass in accordance with this invention;

FIGS. 15 and 16 are flow diagrams of a suitable control program for use with the CPU of FIGS. 4-10;

FIG. 17 is a diagram of another circuit for generating the AGC amplifier and integrator channels; and FIGS. 18, 19a and 19b illustrate a program sequence which searches for air leaks and then searches for separations in two eight-channel groups.

Figure 1:
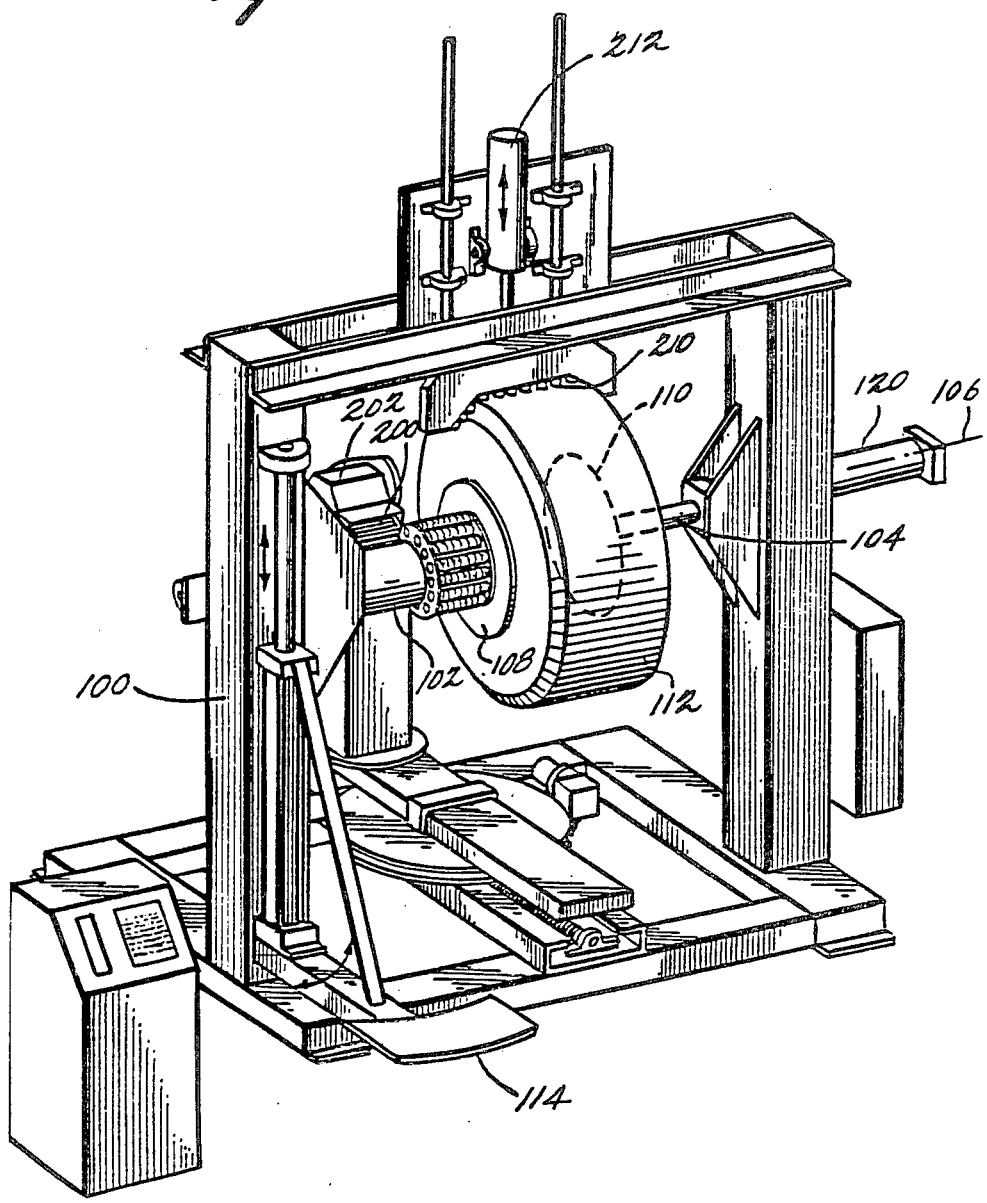
FIGS. 1 and 2 are perspective views of a combined NDI/buffer machine constructed in accordance with this invention.
Figure 2:
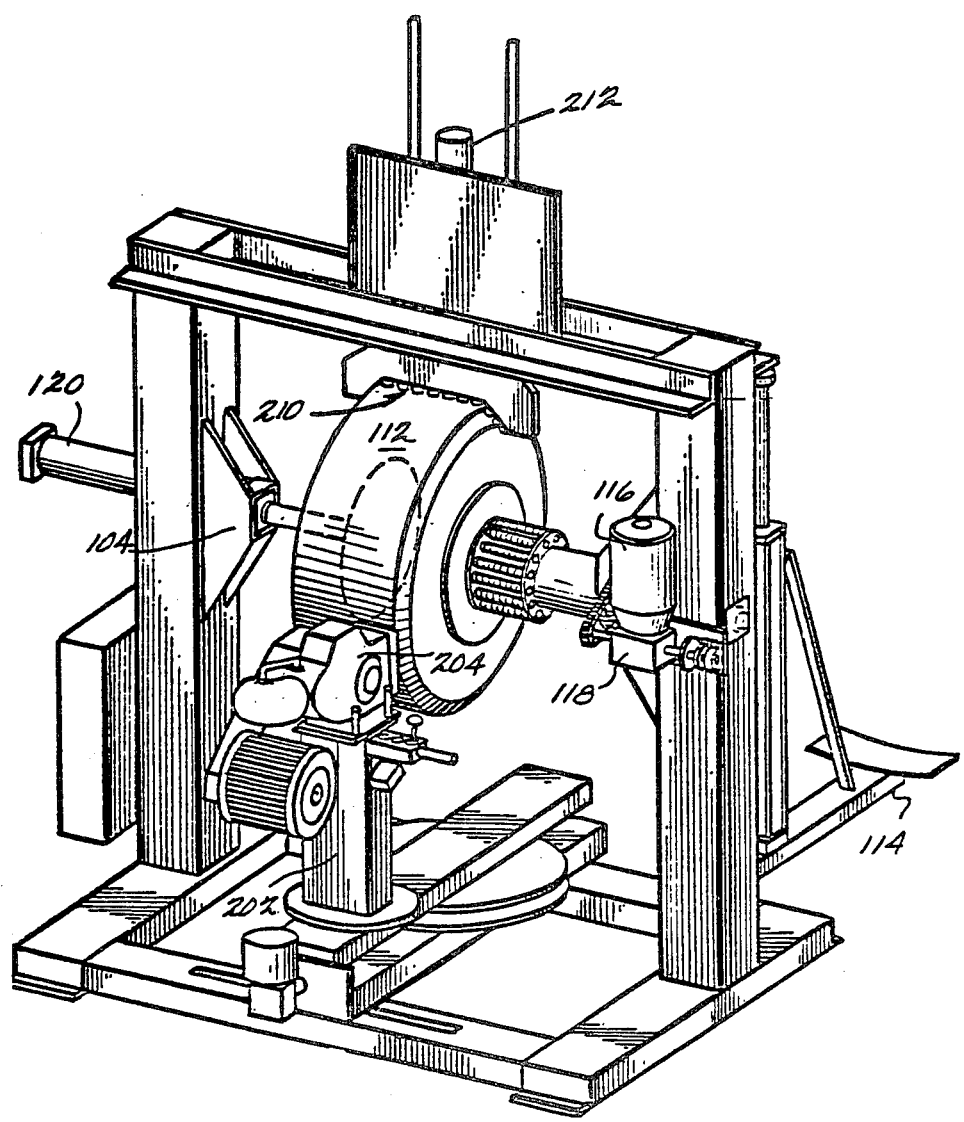

Referring to FIGS. 1 and 2, two perspective view of the presently preferred exemplary combined tire buffer and NDI machine are shown. As will be apparent, the NDI features of the machine may be provided, if desired, without including the tire buffing capability.

The major mechanical components of the machine are mounted to an open frame 100 having a fixed spindle 102 and an axially movable spindle 104 opposingly aligned along horizontal axis 106. Conventional circular tire counting rings or flanges 108 and 110 are attached to the outer rotatable ends of spindles 102 and 104 for mounting an inflated tire 112, therebetween. A conventional pneumatically operated tire lift mechanism 114 is conveniently provided so as to assist the human operator in lifting and swinging a tire into and out of place between rings 108 and 110 during tire mounting and demounting operations.

Ring 108, and hence tire 112, is driven by a two horsepower d.c. motor 116 through reducing gears 118. A tire surface speed of approximately 600 feet per minute is preferred for buffing operations while a much lower speed of approximately 40 feet per minute is preferred for NDI operations. Spindle 104, and hence ring 110, is axially extended and retracted by pneumatic cylinder 120. During tire mounting operations, ring 110 is retracted by cylinder 120 so as to permit the tire 112 to be lifted into place on ring 108 by lift 114. Thereafter, ring 110 is extended against the corresponding rim of tire 112 and the tire is inflated to a desired set point pressure by compressed air passed through the center of spindle 102.

A conventional rotating tire buffing rasp 200 is mounted on a vertical pedestal 202 situated on the backside of the machine as seen in FIG. 2. The rasp 200 is controlled via a conventional panel 204 to move laterally along a desired buffing path 206 and horizontally towards and away from the tire by conventional control mechanisms including a "joy stick" used to control pneumatic cylinder 208, lead screws and associated drive motors and the like. The buffer rasp 200 is rotated by a separate motor mounted on pedestal 202. The buffer mechanism, per se, is of a conventional type as marketed by Bandag, Inc., e.g. Buffer Model No. 23A.

An array of 16 ultrasonic acoustic receiving transducers 210 is disposed above and around the outer walls of tire 112. The receivers 210 preferably include a conically shaped collimator and/or focusing tube to help limit the field of view for each individual transducer to a relatively small and unique area across the tire wall. The receivers 210 may be conveniently potted either individually or in groups in a polyurethane foam or the like to help mechanically fix the receivers in their respective desired positions, to help protect the receivers and to help isolate the receivers from spurious ambient acoustic signals. The array of receivers 210 is radially adjusted into operative position by an air cylinder 212 having a coupled hydraulic control cylinder so as to define a radially extended operative position for the receivers 210.

Figure 3:
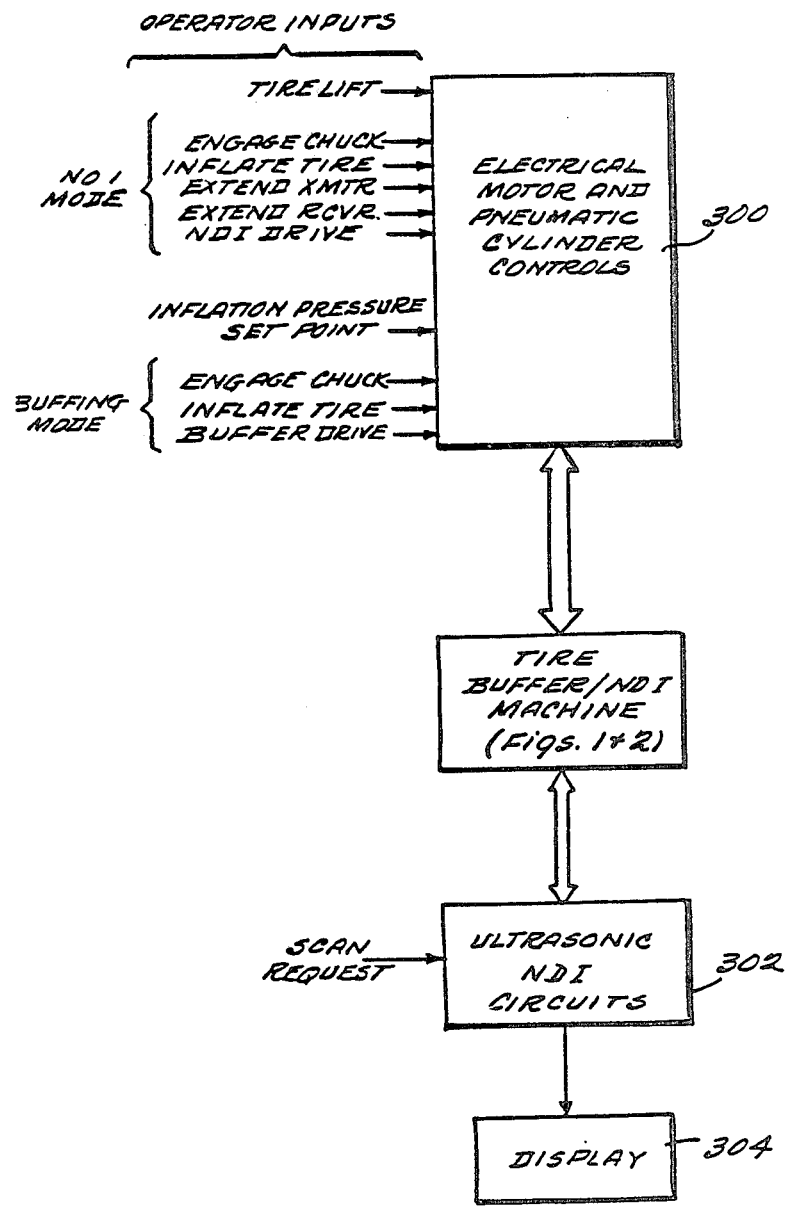
FIG. 3 is a block diagram of the invention shown in FIGS. 1 and 2.

A block diagram of the combined tire buffer/NDI machine and its associated electrical and pneumatic circuits is shown in FIG. 3. The electrical motor and pneumatic cylinder controls 300 are of entirely conventional design and thus not shown in detail. Operator inputs depicted at the left of FIG. 3 are made directly or indirectly by the operator via conventional electrical switches, relays, air valves and/or liquid control valves.

In operation, a tire is placed on lift 114 and raised into position between the rings 108 and 110. Preferably, a predetermined index position on the tire is aligned with a physical index position on flange 108. Thereafter, the chucking apparatus is engaged by causing flange 110 to move into the tire 112 so as to pinch the tire beads together in preparation for tire inflation. The tire is then inflated to a desired set point pressure. The flange 108 is spring-loaded such that during chuck engagement and tire inflation, it is caused to move axially outwardly against the spring-loaded (e.g. by approximately 2 inches). This facilitates the tire inflation process and simultaneously uncovers an ultrasonic transmitter located within the tire from a relatively protected position so that it may subsequently be extended into an operative position under the array of receivers 210. An interlock switch activated by air pressure and/or by the physical movement of flange 108 may be used to prevent any premature extension of the transmitter before it is uncovered from its protected position.

In the buffing mode, the transmitter need not be extended. The buffig rasp drive motors are conventionally activated and controlled (e.g. with a "joy stick" and conventional push button controls) to buff the tire tread surface as desired. Although it may not be required, it is presently preferred to have the tire buffed to a substantially uniform outer treadwall surface before NDI operations are performed. Such buffing is believed to avoid possible spurious indications of defects caused by normal tread patterns and/or by uneven wear about the tire surface.

When the operator selects the NDI mode of operation, an ultrasonic transmitter located inside the inflated tire 112 is extended into operative position and the array of receivers 210 is lowered into operative position by respectively associated pneumatic cylinders. The same 2-horsepower d.c. motor which drives the tire at approximately 600 surface feet per minute during buffing operations may be reduced in speed by conventional electrical circuits so as to drive the tire at approximately 40 surface feet per minute during the NDI mode. After the tire motion has reached a steady state, the operator may activate the scan request input switch to the ultrasonic NDI circuits 302. Thereafter the walls of tire 112 will be ultrasonically inspected during one or more complete tire revolutions to produce a display 304 which can be humanly interpreted directly or indirectly to reveal the condition of the tire (e.g., satisfactory for further buffing and retreading, doubtful or unsatisfactory). If questionable condition is indicated, the tire may be discarded or may be additionally buffed and retested.

The ultrasonic NDI circuits 302 are shown in greater detail at FIGS. 4–10. As shown in FIG. 4, the outputs from the 16 ultrasonic receivers 210 are amplified and multiplexed onto eight signal processing channels A-H by circuits 402 which are shown in greater detail in FIG. 5. Each signal processing channel then provides AGC amplification, rectification, integration and analog-to-digital conversion with the signal processing circuitry 404. A representative channel of such processing circuitry is shown in detail at FIG. 7. The resulting digitized outputs are presented to a conventional eight bit data bus 406 which is interconnected to a conventional micro-computer CPU (e.g. an 8080 type of eight bit computer) 408. The CPU 408 is also connected via a conventional address bus 410 and data bus 406 to a data memory 412, to a programmable read-only memory (PROM) 414 and to a system interface circuit 416 which is shown in detail at FIG. 8. A display interface 418 (shown in detail at FIG. 10) is directly connected to the data memory banks 412 to provide a CRT type of oscilloscope display.

The system interface 416 provides the necessary gating and other control signals to the signal processing circuitry 404 and also provides HIGH CHAN multiplexing signals to the preamplifier circuits 402 as well as to the transmitter drivers and multiplexing circuitry 422 used to drive plural ultrasonic transmitters. The operation of the entire system is synchronized to the rotational movements of tire 112 through a rotary pulse generator 424 directly driven with the tire (e.g. geared to the reducer gears). The rotary pulse generator 424 provides 1,024 pulses per revolution at terminal RPGX and 1 pulse per revolution at terminals RPGY.

As shown in FIG. 5, ultrasonic acoustic transmitting crystals 500 and 502 are disposed inside inflated tire 112, which is chucked between rings 108 and 110, rotatably secured to spindles 102 and 104, respectively. The electrical leads feeding transmitters 500 and 502 are fed out through the fixed spindle 102 to the transmitter activation circuits. Inflation air is likewise fed in through the center of spindle 102 as are pneumatic lines and/or other control connections for extending and retracting the transmitters.

The exemplary ultrasonic transmitters 500 and 502 have a radiation field which substantially illuminates a sector of approximately 90°. Hence, they are mounted at 90° with respect to one another on block 504 which may, for example, be formed from polyvinyl chloride plastic materials. It has been found that acceptable operation will not result if the transmitters are too close to the inside tire surfaces or too far away from these surfaces. In the preferred exemplary embodiment, transmitting crystals 500 and 502 are approximately two inches from the inner tire wall surfaces although this optimum distance of separation may be varied by a considerable amount (e.g. plus or minus approximately one inch).

The arrayed receiving transducers 210 are located about an arc generally corresponding to the outside shape of the tire wall. Here again, it has been found that acceptable operation does not result if the receivers are too close or too far away from the outer tire walls. Preferably, the receivers are no closer than approximately 1 inch to the outer tire surface but are preferably within 5.5 to 8.5 inches of the opposingly situated transmitting crystal. The receiving transducers 210 preferably each employ a conically shaped collimator and/or focusing tube as shown in detail at FIG. 12. These tubes are preferably machined from polyvinyl chloride plastic material and also help to match the impedance of the actual transducer crystal surface to the surrounding ambient air acoustic impedance.

A moderately high ultrasonic frequency is employed so as to help avoid interference from spurious ambient acoustic signals and to obtain increased resolution by using shorter wavelength acoustic signals while at the same time avoiding ultra-high frequency acoustic signals and the problems associated therewith. Frequencies above 40 kHz are desirable with 75 kHz being chosen as the presently preferred optimum frequency. Ultrasonic transducing crystals operating at 75 kHz are conventionally available. For example, receiving crystals are available as the MK-111 transducer from Massa Corporation, Windom, Mass., having the following specifications:

| | |
|---|---|
| Frequency of Maximum Impedance (fm) | 75 kHz ± 3 kHz |
| Impedance at fm (min | 6K Ohms |
| Receiving Sensitivity (O.C.) at Frequency of Max Output Db re 1 Volt/microbar | −70DB min. |
| Transmitting Sensitivity Db re 1 microbar at 1 ft./10mw | −12DB Min. |
| Maximum Power Input | 100MW |
| Directivity | −10DB Max. at 90° Total Angle |
| Temperature Stability | 10% Change in Frequency −30° F. to +150° F. |
| Capacitance | 1200 ± 20% PF |

A suitable transmitting crystal tuned to approximately 75 kHz is available from Ametek/Straza, California under No. 8-6A016853.

The electrical leads from each of the transducers 210 are preferably connected through coaxial cables 506 to their respectively associated pre-amplifiers 508. The outputs from each of the 16 amplifiers 508 are connected to an eight pole double throw electronic switch comprising Signetics SD5000 integrated circuits, controlled by the HIGH CHAN multiplexing signal provided by system interface 416. The eight resulting multiplexed output channels are connected through transistor buffer amplifiers to signal processing channels A-H. Accordingly, in the absence of a HIGH CHAN multiplex signal, the outputs from the first eight preamplifiers 508 are coupled to respectively corresponding signal processing channels A-H. However, when the HIGH CHAN multiplexing signal is present, the outputs from the last eight of the pre-amplifiers 508 are connected to respectively corresponding signal processing channels A-H.

The circuitry of each pre-amplifier 508 is shown in more detail at FIG. 6. It includes a first transistorized stage having a gain of approximately 150 followed by a cascaded integrated circuit amplifier having a gain factor of approximately 11.

The signal processing circuits 404 for each of channels A-H are identical. Accordingly, only the circuitry for channel A is shown in FIG. 7. The waveforms shown in FIG. 11 will be useful in understanding the operation of the circuitry in FIG. 7.

The generation of a pulsed or bursted ultrasonic waveform for driving the transmitters 500 and 502 will be described later. However, by reference to FIG. 11, it may be seen that each transmitter is driven to provide at least one approximately 50 cycle burst of 75 kHz acoustic output signals each time an RPGX trigger pulse occurs (e.g. 1,024 times per tire revolution). After a transmission delay, which will depend upon the separation between transmitter and receiver and the characteristics of the intervening ambient air and tire rubber, the transmitted acoustic signals are received. The received and transduced acoustic signals may have a complex amplitude envelope (rather than the well-behaved one shown in FIG. 11) depending upon the type of multiple reflections, internal reverberations, wave cancellations, and/or other peculiar wave effects which take place along the transmission path. Accordingly, it is only the leading edge or initial portion of each such ultrasonic pulse or burst (e.g. where the amplitude envelope is initially increasing) that provides the best and most accurate indication of the transmission path quality (i.e. its included tire structural defects). Accordingly, the signal processing circuitry shown in FIG. 7 is adapted to effectively utilize only such initial or leading edge portions of each burst of ultrasonic signals. In one embodiment, data for each tire measurement area is obtained by averaging measurements taken at different respective acoustic frequencies.

As explained in U.S. Pat. No. 3,882,717, it is necessary to provide automatic gain control amplification of through-transmission ultrasonic test signals to compensate for different average tire casing thicknesses. This earlier patented system had but a single signal processing channel with AGC employed to compensate for differences in average tire casing thicknesses over the cross-section of a given tire. However, it has been discovered that automatic gain controlled amplification must also be included in each of the plural testing channels of this invention so as to compensate for differences in average tire casing thickness from tire-to-tire.

Accordingly, an AGC amplifier 700 (e.g. integrated circuit MC1352) is included within channel A as shown in FIG. 7. The ultrasonic signals passing through channel A are fed back to pin 10 of the AGC amplifier 700 and input to a relatively long time constant (e.g. 10 seconds) RC circuit 702 connected to pin 9 of amplifier 700. Accordingly, the average of signals passing through the channel over the last several seconds (during the included periods that the amplifier is enabled) is compared to a constant reference AGC bias presented at pin 6 so as to maintain a substantially constant average output level at pin 7 over the RC time constant period. Amplifier 700 in the preferred exemplary embodiment has a gain which may vary automatically between a factor of 1 and 1000.

Amplifiers 704 and 706 are connected in cascade within channel A and each provide a gain factor of approximately 2. Additionally, amplifier 706 has diodes 708 and 710 connected so as to effect a full wave rectification of its output signals as presented to the FET gate 712.

Referring back to FIG. 11, an integrate reset signal INTGRST is generated during the first transmission delay period for a given test tire position and presented to FET gate 714 (FIG. 7) so as to discharge the integration capacitor 716 connected across amplifier 718 (forming a Miller-type integrator). Furthermore, the AGC amplifier 700 is enabled by the $\overline{\text{AGCEN}}$ signal at some point during each testing cycle so as to sample the received signals. The integrator enabling signal $\overline{\text{INTGEN}}$ is timed so as to enable the FET switch 712 only during the initial portions or leading edge of the ultrasonic burst (e.g. approximately 130 microseconds or about the first 10 cycles of the 75 kHz burst). If desired, two or more received bursts at respective different frequencies may be sampled and the results integrated together so as to effectively average measurements taken at different frequencies (and hence having different acoustic standing wave patterns).

Thereafter, the output of integrator 718 is converted to a digital signal under program control by CPU 408 generating suitable analog DAC inputs to comparator 720 and conversion gating signals CONV to gate 722 which interfaces with one of the conventional data bus lines (in this case $\overline{\text{DB}\phi}$. Such program controlled analog-to-digital conversion is conventional and involves the CPU program controlled conversion of reference digital signals to reference analog DAC signals which are then successively compared in comparator 720 with the results of such comparisons being made available to the CPU via data bus lines and gates 722. By a process of successive comparisons to different known reference signals, the programmed CPU is capable of determining a digital value corresponding to the input integrated analog value from amplifier 718.

This process is of course repeated simultaneously in channels A-H and successively in each channel for each burst or group bursts of ultrasonic signals occurring at a given tire wall test site.

Figure 8:
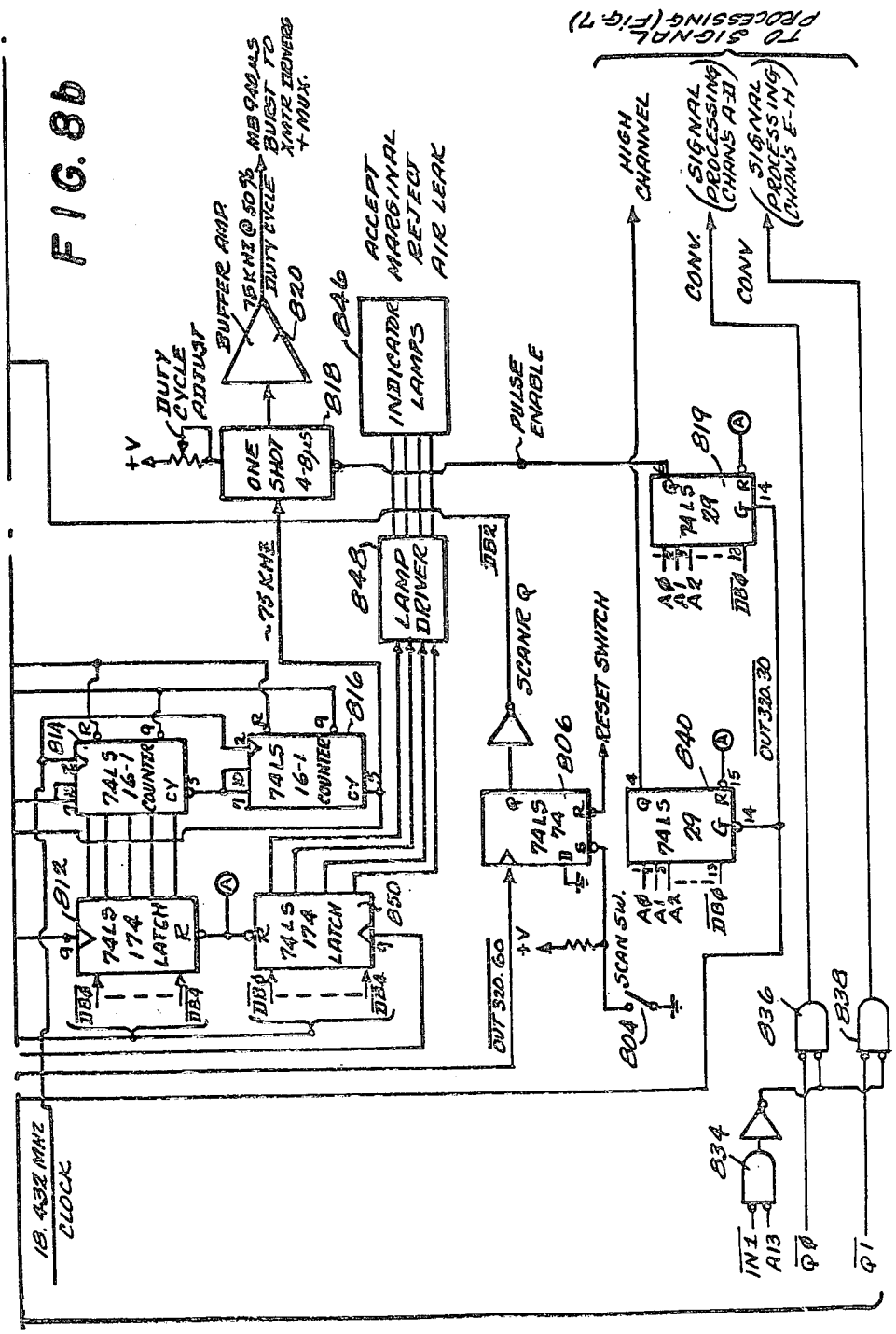

Referring now to FIG. 8, the RPGX (1,024 pulses per revolution) and RPGY (1 pulse per revolution) signals from the rotary pulse generator are passed through tri-state buffers 800 to data bus lines $\overline{\text{DB0}}$ and $\overline{\text{DB1}}$ respectively in response to the $\overline{\text{IN3}}$ and $\overline{\text{Q4}}$ addressing signals provided by the CPU. Other addressing outputs from the CPU are input to an output decoder 802 so as to provide signals $\overline{\text{OUT320.00}}$ through $\overline{\text{OUT320.70}}$ under appropriate program control.

Just prior to a scan cycle, the CPU is programmed to repetitively poll data bus line $\overline{\text{DB2}}$ looking for a scan request signal $\overline{\text{SCANRQ}}$ generated by an operator manipulation of the scan request switch 804 which causes flip-flop 806 to be set at the next occurrence of $\overline{\text{OUT320.60}}$.

Once a scan request has been detected by the CPU via data bus line $\overline{\text{DB2}}$, the CPU is programmed to poll the RPGX and RPGY signals which are then presented on data bus lines $\overline{\text{DB}\phi}$ and $\overline{\text{DB1}}$ by address inputs $\overline{\text{IN3}}$ and $\overline{\text{Q4}}$. An actual measurement cycle is not started until the second RPGY signal is detected so as to insure that the tire is running true at a substantially steady state speed and that the AGC circuits are operating properly. Thereafter, each occurrence of an RPGX signal detected by the CPU is programmed to cause the generation of an $\overline{\text{OUT320.10}}$ signal. The $\overline{\text{OUT320.10}}$ signal triggers one shot circuits 808 and 810 and also enables the latch 812 to accept the digital values presented on data bus lines $\overline{\text{DB}\phi}$ through $\overline{\text{DB4}}$.

Just prior to the generation of the first burst of ultrasonic waves at a given tire wall test site, the CPU generates $\overline{\text{OUT320.70}}$ which triggers reset one shot 822 and provides an integrator reset signal INTGRST via addressable flip-flop 823 and NAND gate 825.

The 4 bit binary counters 814 and 816 are connected in cascade to count the 18.432 Mhz clock signals input from the CPU board and to divide these clock pulses by a numerical factor represented by the contents of latch 812. The result is an approximately 75 kHz clock signal, (both 74 kHz and 76 kHz frequencies are used successively in one embodiment with the two results averaged together) which is used to trigger one shot 818 having an adjustable time period such that its output can be adjusted to a substantially square wave 50% duty cycle signal. As shown in FIG. 8, one shot 818 is controlled by a pulser enabling signal from the addressable flip-flop 819. Thus if desired (e.g. to listen for leaks), the ultrasonic transmitters may be selectively disabled by the CPU.

The approximately 75 kHz 50% duty cycle signal is then buffered through amplifier 820 and presented as square wave output MB (see FIG. 11) to conventional transmitter driver amplifiers (providing approximately 200 volts peak-to-peak electrical output) which, in turn, cause a generally sinusoid type of 75 kHz acoustic output from the transmitter as shown in FIG. 11.

This generation of the approximately 75 kHz output MB will continue until one shot 808 times out (e.g. approximately 1 millisecond). During that interval, a burst of ultrasonic acoustic signals is caused to emanate from one of the transmitting crystals.

The period of one shot 810 is adjusted for a delay approximately equal to but slightly less than the transmission delay between acoustic transducers. The delayed output from one shot 810 resets the data ready flip-flop 828 and triggers the integrate timing one shot 826 which produces the integrate enable signal INT-GEN. At the conclusion of the integrate enable signal from one shot 826, the data ready flip-flop 828 is set to provide a data ready signal to the CPU via data bus line $\overline{DB4}$. If more than one analog data value is to be combined at the output of the integrator, the CPU is simply programmed to ignore the data ready signal until the requisite number of measurement cycles have been completed. Ultimately, however, the data ready signal indicates to the CPU that analog-to-digital conversion of the integrated analog signal is now ready to be performed. The CPU, under conventional program control, then begins to produce various analog reference signals DAC from the digital-to-analog converter 830 under control of the digital data latched into latch 832 from the data bus lines by the addressing signal $\overline{OUT320.00}$. At the same time, the CPU is programmed to provide proper conversion gating signals CONV via the addressing inputs to gates 834, 836 and 838.

The DAC may be a linear type 08 or a non-linear exponential type 76 or other known non-linear types of DAC circuits. The non-linear DAC-76 is believed to improve the effective signal-to-noise ratio for lower level signals.

The CPU is programmed so as to normally produce the multiplexing HIGH CHAN output by setting and resetting the addressable flip-flop 840 via the address lines A$\phi$-A2, $\overline{OUT320.30}$ in accordance with the data value then present on data line $\overline{DB\phi}$. However, manual override switch 842 has been provided so that either the low channels $\phi$-7 or high channels 8-15 may be manually forced via tri-state buffers 844 with outputs connected to the data bus lines $\overline{DB6}$ and $\overline{DB7}$.

The flow diagram for an exemplary CPU control program is shown in FIGS. 15-16. Conventional power-up, resetting and initialization steps are shown at block 1500. After the START entry point, the scan request flip-flop 806 (FIG. 8) is reset, the integrators are disabled (via flip-flop 823, FIG. 8), and the data memory circuits are disabled at block 1502. Thereafter polling loop 1504 is entered and maintained until a SCANRQ on DB2 is detected.

Once a scan request has been detected, the indicator lamps are tested, the integrators are enabled for normal operation (via flip-flop 823), the data memory is enabled for access by the CPU (and conversely, the display interface is disabled from access to the data memory) at block 1506. The high/low/normal switch 842 (FIG. 8) is also checked via DB6 and DB7. If the low or normal mode is indicated, the HIGH CHAN multiplex signal is maintained equal to zero via flip-flop 840. Thereafter, polling loop 1508 is entered to test for an RPGY transition. A similar polling loop 1510 is subsequently entered to issue at least one tire revolution before measurements are taken. Then a software counter $\theta_{current}$ is set to zero and the LOOP1 testing subroutine (FIG. 16) is entered.

As will now be explained in more detail, the step within LOOP1 are executed 1024 times to collect and record 1024 data values in each of eight transducer channels corresponding to 1024 tire testing sites distributed over a whole 360° of tire rotation in each of the eight channels.

After entry of LOOP1, the RPGX signal on DB$\phi$ is tested for a transition from 1 to $\phi$ at loop 1600. Once this transition occurs, all the integrators are reset (via one shot 822, FIG. 8), the latch 812 is set to produce a 74 kHz MB drive signal and the transducers are driven with a burst of 74 kHz MB drive signals via one shot 808 and a pulser enabling signal via flip-flop 819. Since one shot 810 is also triggered, the leading edge of the received burst is gated and integrated in each channel.

While this test at 74 kHz is being performed, the CPU is in a wait loop 1602. Thereafter, latch 812 is reset to produce a 76 kHz MB signal and the transmitters are again pulsed. The result is another gated integration of the leading edge of a received burst at 76 kHz. As soon as this second integration is completed, the data ready signal on DB4 is detected at waiting loop 1604. After the analog data has thus been accumulated for two different frequencies at a given tire test site, the AGC circuits are keyed (to keep them actively sampling the channel signal level within the relevant RC time constant period) and a conventional analog-to-digital conversion routine is entered. This routine converts each integrator output to a six bit digital value which is then stored in the data memory 412. The data for each channel is stored in a separate section of the memory so that similar data points fof each channel can be later addressed using the same lower order memory addressing signals.

The $\theta_{current}$ software counter is thereafter incremented by one and LOOP1 is re-entered unless data measurements at all 1024 tire test sites have already been taken.

After the first exit from LOOP1, a pattern recognition subroutine may be entered, if desired, at block 1512. The pattern recognition results may then be tested at 1514 and 1516 to determine which of status indicator lamps 846 (FIG. 8) should be lighted. Alternatively, the pattern recognition steps may be skipped as shown by dotted line 1518 to flip the HIGH CHAN multiplex signal, if operation is in the normal mode. (If only high or low channel testing has been forced by switch 842, return can now be made to the START entry point.) Thereafter, measurements are taken for the higher group of eight channels as should now be apparent.

While LOOP1 in FIG. 16 causes measurements at 74 KHz and 76 KHz to be combined, it should also be apparent that block 1606 can be skipped if measurements at only a single frequency are desired. Similarly, measurements at more than two frequencies can be combined if desired. Furthermore, the combination of plural data values can be initially made either in analog form (as in the exemplary embodiment) or in digital form as should now be apparent.

As already discussed, the cpu may be programmed, if desired, to automatically analyze the digitized data collected during a complete scanning cycle with pattern recognition algorithms and to activate one of the indicator lamps 846 (e.g., representing acceptance, rejection or air leakage) via conventional lamp driving circuits 848 as controlled by the contents of latch 850 which is filled from data bus lines $\overline{DB\phi}$ through $\overline{DB4}$ under control of the address generated $\overline{OUT320.20}$ signal. Air leakage can be detected, for example, by performing a complete scanning and measurement cycle while disabling the ultrasonic transmitters. Detected increases in received signals are then detected as leaks.

The central processing unit shown in FIG. 9 is conventionally connected to decode the various address lines and provide addressing inputs already discussed with respect to the system interface shown in FIG. 8. The CPU itself is a conventional integrated circuit 8080 microprocessor having data input and output lines D$\phi$ through D7 which are connected to the data bus lines $\overline{DB\phi}$ through $\overline{DB7}$ through conventional bi-directional bus driver circuits 900. Address lines A$\phi$ through A9 and A13 are also directly connected through buffer amplifiers 902 to the system interface, memory circuits, etc. Address lines A10, A11 and A12 are decoded in decoder 904 to provide addressing outputs $\overline{Q\phi}$ through $\overline{Q7}$. Similarly, addressing lines A14 and A15 are decoded together with the normal writing and data bus input signals from the CPU in decoder circuitry 906 to provide $\overline{IN\phi}$ through $\overline{IN3}$ and $\overline{OUT\phi}$ through $\overline{OUT3}$ addressing outputs. The normal data bus input CPU signal DBIN and the addressing lines 814 and 815 are also connected through gates 908 and 910 to conventionally provide a directional enabling input to the bi-directional bus drivers 900. The approximately 18 Mhz clock 912 is also conventionally connected to the 8080 CPU. However, pin 12 of the 3G8224 integrated circuit is brought out to deliver an 18.432 Mhz clock to the frequency dividing circuits of the system interface already discussed with respect to FIG. 8.

The data memory circuits are provided by a conventional connection of 25 integrated circuits of the 4045 type so as to provide 8,192 eight bit bytes or words of data storage capability.

The programmable read-only memories may be provided by three integrated circuits of the 2708 type, each providing 1,024 bytes of programmed memory. 256 eight bit words of read/write memory are also preferably connected to the CPU as part of the programmable memory circuits. An integrated circuit of the type 2111-1 may be used for this purpose.

The CRT display interface is directly connected to the data memory board. Once an entire measure cycle has been completed (e.g. when the third RPGY signal has been detected after a scan request), there are 1,024 data values available for each of the 16 measurement channels representing the relative magnitudes of ultrasonic signals transmitted through the tire at 1,024 successive respectively corresponding positions about the tire circumference within the area monitored by the receiving transducer for a given channel. This digital data may be converted to conventional video driving signals for a CRT and displayed as shown in FIGS. 13 and 14. Alternatively, the 8080 computer may be programmed to analyze (e.g. by pattern recognition algorithms) the available digital data and to activate appropriate ones of the indicator lamps 846 shown in FIG. 8.

The display interface shown in FIG. 10 is conventionally connected directly to the data memory 412 via memory data bus lines 1000, memory quadrant selection bus lines 1002, memory address bus lines 1004 and data latch strobe line 1006. The whole display can be selectively disabled or enabled as desired under CPU control via CPU addressing outputs A13, $\overline{Q3}$, $\overline{OUT3}$ and A$\phi$ via flip-flop 1008 and the associated inverter and gates shown in FIG. 10. In the preferred embodiment, the display interface is disabled whenever other parts of the system are accessing the data memory 412 so as to prevent possible simultaneous activation of the data memory circuits.

The display interface is driven by a 11.445 MHz clock 1010. Its output drives counter 1012 which is connected to divide the clock signals by a factor of 70. The first 64 counts of counter 1012 are used by comparator 1014 which also receives 6 bits of data (i.e. 64 different numerical values) from the addressed data memory location representing the magnitude of ultrasonic signals transmitted through a particular tire testing site. Thus the output from comparator 1014 on line 1016 will occur at a specific time within 64 clock periods corresponding to the magnitude of the input digital data via lines 1000. The clock pulse during data coincidence will cause flip-flop 1018 to transition momentarily and produce a video output pulse via gate 1020 having one display dot time width and spaced within its respectively corresponding channel time slot according to the magnitude of the recorded data. Flip-flop 1022 is triggered by counter 1012 upon counting a 65th clock pulse and generates an inter-channel separation blanking video pulse out of gate 1020. The counter 1012 then continues to count 5 more clock pulses before resetting itself and starting another cycle using data from the next adjacent channel.

The 70th count from counter 1012 also drives a three bit channel counter 1024 which, through the 3-to-8 decoder 1026, successively addresses eight different sections of the data memory corresponding respectively to eight of the sixteen ultrasonic receiver channels. A selection between display of the higher or lower eight channels is made via switch 1028.

At the end of a complete horizontal scan line, 8×70 clock pulses (2×70 clock pulses are counted during horizontal retrace period) will have been counted by counters 1012 and 1024 and a carry pulse will go to the 12 bit counter 1029 so as to increment the addresses on line 1004 (via decoder 1030) for the next horizontal scan line. In the case of the usual interlaced CRT scanning raster, every other horizontal line will actually be skipped and picked up during a second vertical seam raster as will be appreciated. The states of counters 1024 and 1029 provide all requisite timing information for conventionally generating the usual CRT horizontal synchronization, vertical synchronization and vertical and horizontal retrace blanking video signals at 1032.

The various video signals are conventionally mixed in video amplifier 1034 and output to a CRT display.

Since there are 1024 data values in each channel but many fewer horizontal scan lines iln the usual CRT raster, switch 1036 is provided so as to select only the odd or even addresses for data values in a given channel. Thus the complete 360° of scanned tire surface, within a given channel, is displayed in an assigned time slot over 512 vertically-spaced horizontal scan lines.

As thus described, the data values for a given channel would be distributed within a vertical segment of the CRT display and displaced in a horizontal sense from a vertical base datum line in accordance with the stored data values. However, in the preferred embodiment, the CRT deflection yoke is rotated by 90° so that the final CRT display for a channel is presented horizontally as shown in FIGS. 13 and 14.

As depicted in FIGS. 13 and 14, the signal traces in each individual channel are deflected upwardly to represent reduced ultrasonic signal magnitudes. Accordingly, in FIG. 13, it can be seen that a defect has occurred in channels 12 and 13 a at approximately 20° from the index marker. Similarly, a defect is shown in FIG. 14 at channels 12, 13 and 14 at approximately 280°.

Although not shown in FIGS. 13 and 14, if a leak had been present, it would have been indicated by an increased signal magnitude which, in the representation of FIGS. 13 and 14, would have resulted in a downward deflection of the signal trace for the corresponding channel.

The tracing for channels $\phi$ through 3 and 12–15 is caused by wire ends, transitions between various normal tire layers and a periodic pattern of remaining tire tread structures about the outer edges of the tire treadwall. The data actually shown in FIGS. 13 and 14 was taken using a linear DAC circuit in the analog-to-digital conversional process.

FIG. 17 shows another circuit for generating the AGC amplifier and integrator channels. The circuit permits generation of INTGEN, AGCEN, INTGRST, and MBT pulses from RPGX pulses at 1605 or simulated RPG pulses from addressable latch 1608 under program control.

When the RPG simulator is enabled, 1608 output labeled 5 is a 50% duty cycle pulse train which is selected by multiplexor 1611 to trigger one-shots 1612 and 1613. One-shot 1612 is triggered by the rising edge of the output of 1611 and times out in 300 ns. One-shot 1613 is triggered by the falling edge of 1611 and also times out in 300 ns.

The outputs of 1612 and 1613 are combined to trigger DELAY one-shot 1614 and MB one-shot 1615. The generation of 75 KHz bursts by 1615, 1620, 1621, 1622 and 1623 has been previously described. DELAY one-shot 1614 triggers INTEGRATE one-shot 1616 and resets DATA READY flip flop 1617.

Flip flop 1617 signals that the analog outputs of the AGC amplifier/integrator channels are ready for digitizing. Flip flop 1617 is only set while RPG is high.

Flip flop 1617 triggers AGCEN flip flop 1619 which is level shifted and sent to the AGC amplifiers.

A delayed RPG signal appears at the output of flip flop 1618 and it is used by the software for synchronizing to tire rotation.

When the simulator is disabled, multiplexor 1611 sends the logical output of 1605 to one-shots 1612 and 1613. The input source for 1611 now comes from the tire-rotation generated RPGX pulses, and the generation of the required outputs, i.e., INTGEN, is accomplished by controlling multiplexor 1611 outputting pulses to one-shots 1612 and 1613.

The sequence of one-shot firings follows the same pattern as described in the previous paragraphs when the RPG simulator is activated.

The DAC comprised of 1624 and 1625 generate an analog voltage used by the CPU for analog-to-digital conversion of the integrated values of received signals.

Decoder 1609, flip flop 1610, register 1627 and lamp driver 1628 perform functions already described. Latch-decoder decoder 1629 and display 1630 provide status information during program execution.

During air-leak detection, PULSEN generated by software at 1608 is low, thus inhibiting MB excitation pulses to the pulser unit by clearing one-shot 1620.

FIGS. 18, 19a and 19b illustrate a program sequence which searches for air leaks then searches for separations in two eight-channel groups.

Blocks 1631 and 1632 initialize states of the system and 1633 selects the RPG simulator to trigger the one-shot timing elements. The RPG simulator switches alternately high and low at a 8 ms rate while the SCAN RQ flip flop is tested in the loop 1634 and 1635. The RPG simulator refreshes the AGC levels so when SCAN RQ becomes active, data acquisition for air leaks can begin immediately.

When SCAN RQ becomes active, the RPG unit is selected in 1636 and data memory enabled in 1637. Subroutine GETDATA is called at 1638 and is detailed in FIGS. 20a and 20b. Next, PATTERN REC is called at 1639, and any air leaks present will be detected and the AIR LEAK lamp will be turned on by 1640 and 1641.

Now the pulser is activated at 1642. Tests for HI-CHAN, LOCHAN only and normal scan are done at 1643, 1644 and 1645.

Subroutines GETDATA and PATTERN REC are called at 1646. Blocks 1647, 1648, 1649 and 1650 test for REJECT/ACCEPT status and decide whether to continue to scan the high channel group. GETDATA and PATTERN REC are called again at 1651 and the tire status is tested again by 1652 and the program returns to CONTINUE via 1653, REJECT status, or 1654, ACCEPT status.

FIGS. 20a and 20b detail the flow of subroutine GETDATA. The position counter, $\theta$ CURRENT is set to zero at 1655. The tire scan begins at the current tire position which is assumed to be the origin. Block 1656 tests for occurrence of the once-per-revolution INDEX pulse and stores $\theta$ CURRENT at location OFFSET. If INDEX is present, then 1657 stores the location in memory.

Block 1658 waits until RPG is zero. When the condition is met, 1659 sets the pulsing frequency to 74 KHz and repeats the INDEX test at 1660 and 1661, and waits until RPG is one at 1662. A new pulsing frequency is selected at 1663.

When a complete RPG cycle has elapsed, the DATA READY flip flop will be set, and 1664 waits for this condition. When DATA READY is true, eight steady state voltages generated by each of the integrators are converted by block 1665 and stored in data memory as raw data. The tire position is incremented and tested for the last data point at 1666. The program continues to acquire data by jumping to the reentry point B. When all points are digitized and stored, the data is justified in memory by 1667 so the data associated to the INDEX point is at the start of the data block.

While only a few exemplary embodiments and only a few variations thereof have been explained in detail, those in the art will appreciate that many other modifications and variations may be made without departing from the novel and advantageous features of this invention. Accordingly, all such modifications and variations are intended to be included within the scope of this invention as defined by the appended claims.

What is claimed is:

1. Tire testing apparatus for detecting air leaks from pressurized tires, said apparatus comprising:
    an ultrasonic transducer for converting ultrasonic vibrations in excess of about 40 KHz into corresponding electrical signals;
    means for mounting and moving the wall of an inflated tire past said ultrasonic transducer; and
    signal processing means connected to said transducer for detecting the presence of ultrasonic signals in excess of about 40 KHz generated by air escaping from a leak in the tire wall.

2. Tire testing apparatus as in claim 1 wherein said ultrasonic transducer and signal processing means detect ultrasonic signals of approximately 75 KHz in frequency.

3. Tire testing apparatus for detecting leaks from a pressurized tire wall, said apparatus comprising:
   an array of plural ultrasonic transducers mounted to simultaneously scan in proximity to corresponding parallel elongated segments of at least a portion of said pressurized tire wall; and
   electrical signal processing circuitry connected to said ultrasonic transducers for detecting respectively associated ultrasonic signals of approximately 75 KHz generated by leaks from corresponding segments of said portion of said pressurized tire wall.

4. Tire testing apparatus comprising:
   tire mounting means for inflating with air and rotatably holding a tire thereon;
   at least one ultrasonic transducer mounted to scan said inflated tire as it is rotated therepast; and
   electrical signal processing means for detecting only electrical outputs having a frequency of about 75 KHz from said ultrasonic transducer caused by air escaping from a leak in said tire as it passes in proximity to said transducer.

5. Tire testing method for detecting air leaks from pressurized tires, said method comprising:
   mounting and moving the wall of an inflated tire past a stationary ultrasonic transducer which converts ultrasonic vibrations in excess of about 40 KHz into corresponding electrical signals; and
   detecting the presence of ultrasonic signals generated by air escaping from a leak in the tire wall only if in excess of about 40 KHz.

6. Tire testing method as in claim 5 wherein said detected ultrasonic signals are approximately 75 KHz in frequency.

7. Tire testing method for detecting leaks from a pressurized tire wall, said method comprising:
   simultaneously scanning in proximity to parallel adjoining segments along at least a portion of said pressurized tire wall with an array of plural ultrasonic transducers; and
   detecting ultrasonic signals of about 75 KHz generated by leaks from said portion of said pressurized tire wall.

8. Tire testing method comprising:
   inflating with air and rotatably scanning said inflated tire with an ultrasonic transducer as it is rotated therepast;
   detecting electrical outputs from said ultrasonic transducer in excess of about 40 KHz caused by air escaping from a leak in said tire as it passes in proximity to said transducer.

9. Tire testing method as in claim 8 wherein said detected ultrasonic electrical signals are of frequency of about 75 KHz.

* * * * *